United States Patent
Wafa et al.

(10) Patent No.: US 8,324,280 B2
(45) Date of Patent: Dec. 4, 2012

(54) TREATMENT OF PROSTATE CANCER WITH DDC INHIBITOR

(75) Inventors: Latif Wafa, Burnaby (CA); Paul Rennie, Vancouver (CA)

(73) Assignee: The University of British Columbia, Vancouver (CA)

( * ) Notice: Subject to any disclaimer, the term of this patent is extended or adjusted under 35 U.S.C. 154(b) by 523 days.

(21) Appl. No.: 12/537,895

(22) Filed: Aug. 7, 2009

(65) Prior Publication Data

US 2010/0048709 A1 Feb. 25, 2010

Related U.S. Application Data

(60) Provisional application No. 61/136,032, filed on Aug. 7, 2008.

(51) Int. Cl.
*A61K 31/197* (2006.01)
(52) U.S. Cl. ........................................ 514/565
(58) Field of Classification Search ................ None
See application file for complete search history.

(56) References Cited

OTHER PUBLICATIONS

Walczak et al. Mayo Clin. Proc., 2007, vol. 82, No. 2, pp. 243-249.*
Gilbert et al. Clin. Cancer Res., 2000, vol. 6, pp. 4365-4372.*
Gilbert et al., Hydrogen peroxide degradation and selective carbidopa-induced cytotoxicity against human tumor lines, Biochemical Pharmacology, 2005, pp. 1159-1166, Elsevier Inc.
Ippolito et al., Linkage between cellular communications, energy utilization, and proliferation in metastatic neuroendocrine cancers, PNAS, Aug. 15, 2006, pp. 12505-12510, vol. 103, No. 33.
Wafa et al., Isolation and identification of L-dopa decarboxylase as a protein that binds to and enhances transcriptional activity of the androgen receptor using the repressed transactivator yeast two-hybrid system, Biochem. J., 2003, pp. 373-383, vol. 375.
Wafa et al., Identification and characterization of Proteins that interact with the androgen receptor to modulate its activity, Aug. 2007, thesis pp. 1-281, The University of British Columbia.
Wafa et al., Comprehensive expression analysis of L-dopa decarboxylase and established neuroendocrine markers in neoadjuvant hormone-treated versus varying Gleason grade prostate tumors, Human Pathology, 2007, pp. 161-170, vol. 38, Elsevier.

\* cited by examiner

*Primary Examiner* — James D Anderson
(74) *Attorney, Agent, or Firm* — Larson & Anderson, LLC

(57) ABSTRACT

Prostate cancer comes in various forms and has proven difficult to treat. Provided herein are various methods and compositions for treating all forms of prostate cancers with dopa decarboxylase (DDC) inhibitors. These dopa decarboxylase inhibitors include carbidopa (α-Methyl-dopahydrazine), MFMD (α-monofluoromethyldopa), NSD-1015 (3-hydroxybenzylhydrazine), Methyldopa (L-α-Methyl-3,4-dihydroxyphenylalanine) or benserazide, and the inhibitors may be used in combination. DDC inhibitors may also be used to inhibit the progression of prostate cancer to androgen-independence and neuroendocrine prostate cancer.

35 Claims, 13 Drawing Sheets

SEQUENCE LISTING

```
<160> NUMBER OF SEQ ID NOS: 6

<210> SEQ ID NO 1
<211> LENGTH: 55
<212> TYPE: DNA
```

```
<213> ORGANISM: Artificial Sequence
<220> FEATURE:
<223> OTHER INFORMATION: DDC forward

<400> SEQUENCE: 1
ggggacaagt ttgtacaaaa aagcaggctt aaacgcaagt gaattccgaa ggaga          55

<210> SEQ ID NO 2
<211> LENGTH: 54
<212> TYPE: DNA
<213> ORGANISM: Artificial Sequence
<220> FEATURE:
<223> OTHER INFORMATION: DDC reverse

<400> SEQUENCE: 2
ggggaccact ttgtacaaga aagctgggtc ctactccctc tctgctcgca gcac           54

<210> SEQ ID NO 3
<211> LENGTH: 41
<212> TYPE: DNA
<213> ORGANISM: Artificial Sequence
<220> FEATURE:
<223> OTHER INFORMATION: DDC mutation forward

<400> SEQUENCE: 3
attcaacttt aatccccaca tatggctatt ggtgaatttt g                         41

<210> SEQ ID NO 4
<211> LENGTH: 41
<212> TYPE: DNA
<213> ORGANISM: Artificial Sequence
<220> FEATURE:
<223> OTHER INFORMATION: DDC mutation reverse

<400> SEQUENCE: 4
caaaattcac caatagccat atgtggggat taaagttgaa t                         41

<210> SEQ ID NO 5
<211> LENGTH: 5
<212> TYPE: PRT
<213> ORGANISM: Artificial Sequence
<220> FEATURE:
<223> OTHER INFORMATION: LXXLL motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 5

Leu Xaa Xaa Leu Leu
1               5

<210> SEQ ID NO 6
<211> LENGTH: 5
<212> TYPE: PRT
<213> ORGANISM: Artificial Sequence
<220> FEATURE:
<223> OTHER INFORMATION: FXXLF motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 6

Phe Xaa Xaa Leu Phe
1               5
```

TREATMENT OF PROSTATE CANCER WITH DDC INHIBITOR

This application claims the benefit of the filing date of provisional application 61/136,032, filed on Aug. 7, 2008, the disclosure of which is incorporated herein by reference.

FIELD OF INVENTION

The present invention relates to the field of cancer. More specifically, the present invention relates to a method and compositions for treating prostate cancer by inhibiting the enzyme dopa decarboxylase (DDC).

BACKGROUND OF THE INVENTION

Prostate cancer may cause pain, difficulty in urinating, erectile dysfunction and other symptoms. However, many men who develop prostate cancer never have symptoms, undergo no therapy, and eventually die of other causes. The walnut-shaped prostate gland surrounds part of the channel that drains the bladder. When enlarged or cancerous it may compress the channel, obstructing the free flow of urine. While the gland's exact function is not fully understood it is susceptible to three common diseases: prostatitis (infection of the prostate), enlargement, called benign prostatic hyperplasia, and cancer. Prostate cancer is a silent disease and often there are no symptoms for months or years, or until the disease has spread. Consequently, about one-half of the cases are discovered only when the cancer has spread to other parts of the body. What could have been curable in an early stage then becomes life-threatening.

The development of prostate cancer may be linked to increased levels of certain hormones. High levels of androgens (male hormones, such as testosterone) promote prostate cell growth, and may contribute to prostate cancer risk in some men. Some researchers have noted that men with high levels of another hormone, insulin-like growth factor-1 (IGF-1), are more likely to get prostate cancer. IGF-1 hormone is similar to insulin, but it works on cell growth, not sugar metabolism. Some recent studies have found that inflammation may contribute to prostate cancer by increasing DNA damage. Inherited DNA changes in certain genes may cause about 5% to 10% of prostate cancers.

Prostate cancer can often be found early by testing the amount of prostate-specific antigen (PSA) in the blood. Prostate cancer may also be found on a digital rectal exam (DRE). Neither the PSA test nor the DRE is 100% accurate. If certain symptoms or the results of early detection tests—the PSA blood test and/or DRE—suggest that you might have prostate cancer, the doctor will do a prostate biopsy to find out if the disease is present.

Prostate cancer can be treated with surveillance, surgery, radiation, chemo-, cryo- and hormonal therapy. Side effects are common and include urinary incontinence and erectile dysfunction. About 90% of men who have had orchiectomy (surgical removal of the testes) have reduced or absent libido (sexual desire) and impotence. Men getting this treatment should be watched and treated for osteoporosis to help prevent broken bones. Some men also experience hot flashes (these may go away with time), breast tenderness and growth of breast tissue, anemia (low red blood cell counts), decreased mental acuity (sharpness), loss of muscle mass, weight gain, fatigue, decrease in HDL ("good") cholesterol and depression.

Androgens, produced mainly in the testicles, stimulate prostate cancer cells to grow. Lowering androgen levels (androgen deprivation therapy, ADT) often makes prostate cancers shrink or grow more slowly. In advanced prostate cancer, however, the prostate eventually becomes insensitive to the hormonal treatment. The tumour grows back and is untreatable. When the tumour becomes androgen-independent, other factors such as insulin-like growth factor will act to stimulate the androgen receptor (AR). Currently there is no consensus as to whether it is best to start ADT early or try to delay it (to delay developing androgen resistance); whether to use continuous or intermittent ADT; or whether to combine several agents or methods to block androgen.

The AR (located on chromosome Xq11-12) is a steroid receptor whose main function is to bind to DNA to regulate gene expression. One of the known target genes of AR activation is insulin-like growth factor I (IGF-1). Although the AR is a nuclear receptor, it is located in the cytosol until activated by binding of either of the androgenic hormones testosterone or dihydrotestosterone. The binding of an androgen to the AR results in a conformational change in the receptor which in turn causes dissociation of heat shock proteins, dimerization, and transport from the cytosol to the cell nucleus where the AR dimer binds to a specific sequence of DNA known as a hormone response element.

The AR is most closely related to the progesterone receptor, and progestins in higher dosages can block the AR. The AR contains common functional domain structures, including an N-terminal domain (NTD) that harbours activation function 1 (AF1), a central DNA binding domain (DBD) and a C-terminal ligand binding domain (LBD) that contains activation function 2 (AF2). The AF2 of the AR-LBD, formed by helices 3, 3', 4 and 12, is a highly conserved hydrophobic surface that is stabilized by ligand-binding and required for co activator recruitment.

Established coactivators of AR that can regulate receptor hormone-binding prior to nuclear translocation include ARA70 and the hsp90 chaperone protein. While hsp90 has been shown to maintain AR in a high affinity ligand-binding conformation, ARA70 has been suggested to change the conformation of cytosolic AR so that it binds and/or retains androgen more easily and also translocates to the nucleus at a faster rate. Moreover, ARA70 was shown to specifically retard the dissociation of steroid hormones, like estrogen (17 beta-estradiol), which is also known to enhance AR activity, without affecting association of hormone with the receptor.

AR mediates transcriptional activation predominantly through its N-terminal domain AF1 and C-terminal LBD AF2 activation functions. The highly conserved AF2 hydrophobic surface in the LBD of AR is stabilized by androgen and required for recruitment of certain coactivators (namely SRC/p160). Binding of androgen to AR is thought to stabilize helix 12 of AF2 to complete the coactivator binding surface, allowing their recruitment and leading to enhanced AR transcription.

Dopa decarboxylase (DDC) is an enzyme that catalyses decarboxylation of L-3,4-dihydroxyphenylalanine (L-dopa or levodopa) into dopamine (DA) and 5-hydroxytryptophan (5-HTP) into serotonin (5-HT). DDC is not the rate-limiting step in the synthesis of dopamine and serotonin. However, it becomes the rate-limiting step of dopamine synthesis in patients treated with L-DOPA (such as in Parkinson's Disease), and the rate-limiting step of serotonin synthesis in people treated with 5-HTPagonists and the like (such as in mild depression or dysthymia).

Catalytic activity of DDC is dependent on the pyridoxal 5'-phosphate (PLP) cofactor molecule, which binds DDC at Lys residue 303 and allows decarboxylation of amino acid substrates through a Schiff base mechanism. In this reaction, $CO_2$ is released from the amino acid substrate α-carbon and the same carbon is protonated to form the amine product. Mutational analysis performed on DDC has highlighted the importance of numerous residues for enzymatic activity, with one of the most essential residues being Lys303. Using the above mechanism, DDC catalyzes the synthesis of DA and 5-HT but has been suggested to also synthesize trace amines from other amino acids, such as tyrosine, phenylalanine and tryptophan.

The cell surface G-protein-coupled receptors (GPCRs) for DA and 5-HT are known to modulate a plethora of signal transduction pathways. The five DA receptor subtypes (D1 through D5) have been grouped into two classes, the D1-like and D2-like receptors. DA activation of the D1-like receptors, D1 and D5, stimulates adenylyl cyclase activity, elevation of intracellular cAMP and PKA activation. Activation of D2-like receptors, D2, D3 and D4, mediate inhibition of adenylyl cyclase, reduction of cAMP and inhibition of PKA. MAPK and Akt are also possible downstream effectors of both D1- and D2-like DA receptor stimulation. Serotonin receptors have been divided into seven subfamilies by convention. These include 5-HT1 through 5-HT7 GPCRs, except for 5-HT3 receptors, which are serotonin-gated ion channels. 5-HT GPCRs can modulate PKA, PKC, MAPK, PI3-kinase and many other signal transduction pathways.

SUMMARY OF THE INVENTION

The present invention is based on the determination by the inventors that dopa decarboxylase (DDC) inhibitors may be used to treat various forms of prostate cancer. These dopa decarboxylase inhibitors include carbidopa (α-Methyldopahydrazine), MFMD (α-monofluoromethyldopa), NSD-1015 (3-hydroxybenzylhydrazine), Methyldopa (L-α-Methyl-3,4-dihydroxyphenylalanine) or benserazide, or a combination of one or more of these.

Included is a method of treating a subject diagnosed with non-neuroendocrine prostate cancer, comprising administering to the subject a therapeutically effective amount of a dopa decarboxylase (DDC) inhibitor. In an embodiment, carbidopa is used. In an embodiment, two or more dopa decarboxylase inhibitors are used. This method is useful in combination with other cancer therapeutic medication or intervention, such as androgen depletion therapy.

Also provided is a composition for treatment of a patient diagnosed with non-neuroendocrine prostate cancer made from a decarboxylase inhibitor and a pharmaceutically suitable buffer.

The invention further provides for the method of inhibiting transdifferentiation of an androgen independent or androgen sensitive prostate cancer cell to a neuroendocrine prostate cancer cell by exposing the cell to a dopa decarboxylase inhibitor.

Also provided is a method of treating a subject diagnosed with prostate cancer, comprising administering to the subject a therapeutically effective amount of at least two dopa decarboxylase (DDC) inhibitors. This cancer may be neuroendocrine or non-neuroendocrine cancer.

There is also provided a method of treating non-neuroendocrine prostate cancer comprising decreasing the affinity of androgen receptors for androgen in prostate cancer cells by administering a pharmaceutically effective amount of a dopa decarboxylase inhibitor to the prostate cancer cells.

In addition, the decarboxylase inhibitor may be used in the manufacture of a medicament for the treatment of prostate cancer.

DETAILED DESCRIPTION

Figure 1A:
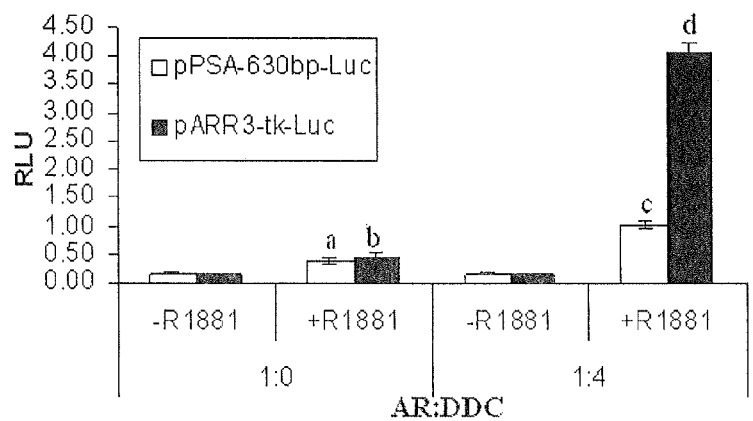
FIGS. 1A-C are bar graphs that depict that DDC enhances AR transcription from the PSA promoter and sensitizes AR to limiting androgen concentrations in PC3 and LNCaP cells.

In order that the invention herein described may be more fully understood, the following description is set forth. One or more embodiments of this invention will be described by way of example. It will be apparent to persons skilled in the art that a number of variations and modifications can be made without departing from the scope of the invention.

Definitions

Any terms not directly defined herein shall be understood to have the meanings commonly associated with them as understood within the art of the invention. As employed throughout the specification, the following terms, unless otherwise indicated, shall be understood to have the following meanings.

As used herein a "subject" refers to an animal, such as a bird or a mammal. Specific animals include rat, mouse, dog, cat, cow, sheep, horse, pig or primate. A subject may further be a human, alternatively referred to as a patient. A subject may further be a transgenic animal. A subject may further be a rodent, such as a mouse or a rat.

"DDC" refers to dopa decarboxylase, also known as L-dopa decarboxylase, aromatic amino acid decarboxylase (AAAD, AADC), tryptophan decarboxylase, 5HT decarboxylase and serotonin decarboxylase.

"DDC inhibitor" refers to any inhibitor or antagonist of DDC, including ones that inhibits DDC enzymatic activity ("DDC-e" inhibitors) and ones that inhibit or prevent the interaction of DDC with the androgen receptor (AR) ("DDC-i" inhibitors). DDC-e inhibitors can be selected from but not limited to the following group: carbidopa (α-Methyl-dopahydrazine), MFMD (α-monofluoromethyldopa), NSD-1015 (3-hydroxybenzylhydrazine), Methyldopa (L-α-Methyl-3,4-dihydroxyphenylalanine) and benserazide.

"Androgen receptor" ("AR") refers to the steroid receptor that is located in the cytoplasm and translocated to the nucleus upon stimulation with androgen or an androgen analogue.

"Androgen depletion therapy" ("ADT"; also known as androgen withdrawal therapy, hormone therapy or hormone-refractory therapy) refers to any therapy used for the treatment of prostate cancer to reduce the levels of the hormone androgen in the subject.

"Androgen independence" ("AI") or "Androgen-Independent prostate cancer" refers to the phenomenon of the prostate cancer showing signs of resistance to or a reduced response to ADT, but still expressing AR. These cells do not depend on androgen to grow. This does not include purely neuroendocrine cancers.

"Androgen sensitive prostate cancer" or "Androgen dependent prostate cancer" refers to prostate cancer cells that depend on androgens for continued cell growth and vitality.

"Transdifferentiation" refers to the ability of a prostate cancer cell to transform into a neuroendocrine state after AR inactivation induced by androgen withdrawal.

"Non-neuroendocrine prostate cancer" refers to prostate cancer where at least some prostate cancer cells have not transdifferentiated to a neuroendocrine state and still express AR and Prostate Specific Antigen (PSA). This refers to both androgen sensitive and androgen independent cells.

"Neuroendocrine prostate cancer" refers to pure neuroendocrine prostate cancer where all cells have fully transdifferentiated to a neuroendocrine state, and neither AR nor PSA are expressed. This type of cancer occurs in only about 1-2% of cases.

"R1881" refers to a synthetic and non-metabolized androgen.

"$B_{max}$" refers to the maximum binding capacity of a receptor; specifically, it refers to the maximum androgen-binding capacity of the androgen receptor.

"Neuroendocrine differentiation" ("NE differentiation") refers to the development of signs of neuroendocrine cells or proliferation of neuroendocrine cells, such as the expression of chromogranin A, bombesin and DDC.

"Treating" refers to performing the method steps of the invention with intention and expectation of a therapeutic benefit to the patient. It would be understood in the art that not all patients respond favorably, or to the same extent to a given treatment. Furthermore, it will be understood in the art that the results of obtained for any individual cannot be compared to results for that individual in the absence of the treatment. Thus, actual therapeutic benefit is not required to fall within the scope of the concept of "treating."

"Inhibiting" refers to the reduction of activity or a process. While full cessation may be desirable, it is not necessary. Any level of reduction to produce treatment is sufficient.

A "therapeutically effective amount" is one that a person skilled in the art would reasonably believe as being capable of treating a patient. This amount may be based on observations regarding the average patient, or may be adjusted based on the characteristics of the individual patient.

A "dosage unit form" may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

"Administered in combination" means contemporaneously, not necessarily instantaneously.

As used herein, the articles "a", "an" or "the" mean one or more, unless the context dictates otherwise.

DDC interacts with the AR in prostate cancer cells and enhances receptor transactivation from a synthetic AR-regulated promoter, an effect that was antagonized by the anti-androgen bicalutamide (Wafa et al. Biochem J. 2003 Oct. 15; 375 (Pt 2):373-83). A notable feature of DDC that may be important for its functional interaction with AR is the presence of an amphipathic alpha-helical LXXLL (SEQ ID NO. 5) motif (amino acids 153-157), which has been shown to be important for docking onto the hydrophobic groove of steroid receptor ligand-binding domains. Although it has been shown that among steroid receptors, the AR-LBD uniquely prefers binding to FXXLF (SEQ ID NO. 6) motifs, one of which is located in the AR-NTD, others have also demonstrated that the AR AF2 binds a subset of SRC LXXLL motifs with high affinity to activate transcription. DDC also contains two additional FXXLL motifs (amino acids 251-255 and 284-288) utilized by nuclear receptor co-regulators to bind receptor ligand-binding domains. The DDC central region containing the LXXLL motif and two FXXLL motifs, are not in involved in binding to AR in vitro. However, it is possible that in the cellular environment, DDC can use these motifs to dock onto the LBD of AR in the cytoplasm.

The literature is unclear on the role of DDC with regards to tumour progression. Certain tumours have shown high levels of DDC expression/activity, including neuroblastoma (Bozzi et al Diagn. Mol. Pathol. 2004; 13: 135-143) and small cell lung cancer (Gilbert et al. Clin. Cancer Res. 2000; 6:4365-72). DDC is one of the proposed biomarkers to detect neuroendocrine (NE) differentiation in prostate (Wafa et al. Hum Pathol. 2007 January; 38(1): 161-70) and other neuroendocrine cancers (Ippolito et al. Proc Natl Acad Sci. 2005 Jul. 12; 102(28):9901-6). DDC is a core component of the transcript signature for tumor cells in a neuroendocrine-transformed transgenic prostate cancer mouse model (Ippolito). Increased neuroendocrine differentiation is one of the hallmarks of prostate cancer (Guate et al, Urol. Int. 1997; 59 (3): 149-53), as well as other cancer-types such as carcinoid cancer, small cell lung cancer and bowel cancer. Once the cancer differentiates in a neuroendocrine fashion, neuroendocrine-phenotype cells can produce mitogenic paracrine and autocrine factors that may mediate tumor growth and survival. Such factors include 5HT (Ishizuka et al. J. Cell. Physiol. 1992;

150: 1-12) (Gattaneo et al. Cancer Res. 1993; 53: 5566-68), the production of which is catalyzed by DDC.

Current therapies for prostate cancer have serious side-effects, and if the cancer has spread beyond the prostate the illness becomes significantly more difficult to treat. Hormonal therapy is one way to try to specifically "starve" only the cancerous cells, however in addition to side-effects it is associated with the risk that the cancer may become more aggressive and resistant to the treatment. The prostate tumour is initially dependent on androgen, and androgen depletion can cure or shrink the cancer. During androgen depletion therapy, the tumour may survive by utilizing factors that can promote cell division in the absence of androgen. The increase in neuroendocrine differentiation during hormone withdrawal was assessed with biomarkers including DDC, chromogranin A and bombesin, and turned out to be dependent on the duration of the therapy (Wafa et al., Hum. Pathol. 2007; 38:161-170).

However, the literature is unclear on the role of DDC inhibitors on tumour progression, in particular prostate tumour progression. Carbidopa, an enzymatic inhibitor of DDC, was lethal to several but not all tested neuroendocrine cancer cell lines, including a carcinoid cancer and a small cell lung cancer cell line (Gilbert et al. Clin. Cancer Res. 2000; 6:4365-72). Even though prostate cancer also is a neuroendocrine-type of cancer, carbidopa did not affect proliferation of a prostate cancer cell line, DU 145 (Gilbert et al. Clin. Cancer Res. 2000; 6:4365-72). DU 145 cells express 5HT 2B- and 4-receptors (Dizeyi et al, Eur. Urol. 2005; 895-900) but not the androgen receptor or only small levels of it (Almirah et al, FEBS Lett. 2006; 580: 2294-2300), suggesting that inhibiting the production of serotonin in itself by DDC is not sufficient to prevent the effect of DDC in prostate cancer. A cocktail of carbidopa, amiloride and flumazenil, targeting $GABA_A$ receptors and GABA metabolism, lead to significant reduction in growth of a pure neuroendocrine tumour (Ippolito et al. Proc Natl Acad Sci. 2006 Aug. 15; 103(33): 12505-10). It would be reasonable to expect that to prevent the effect of DDC on prostate cancer, one would have to interfere with or prevent the interaction between DDC and the androgen receptor. There is no data available that would suggest whether carbidopa would inhibit the interaction between DDC and the androgen receptor. Furthermore, it is unclear what types of compounds would inhibit the interaction between DDC and the androgen receptor. Altogether it is not known what types of compounds would inhibit androgen receptor-driven transcription during androgen depletion therapy and low androgen levels.

The most effective means of treating advanced prostate cancer is by androgen depletion therapy (ADT), which results in temporary regression of prostate tumours but generally leads to androgen-independent (AI) disease. AI is a major problem in the treatment of prostate cancer as the tumour can grow and disease progress in the absence of androgen, drastically reducing the power of ADT. In humans ADT causes a 90% reduction in the level of circulating androgens; the remaining 10% of male hormones are produced from other sources, including the adrenal gland. The low concentrations of this hormone in humans from adrenal secretions may stimulate androgen receptor (AR) transcriptional activity. DDC is a co-activator of the AR, and data provided in the examples demonstrates that DDC sensitizes AR to low androgen levels in prostate cancer cells (Example 1). This suggests that DDC may allow for enhanced AR activity and continued expression of AR-regulated genes involved in tumour growth. Such inappropriate continued activation of AR, despite hormone ablation therapy, may be a critical factor for the cancer cell to develop AI. Furthermore, these examples demonstrate that DDC can function as a coactivator of AR in vitro (Examples 1-3) and in vivo (Examples 8-10); that DDC sensitizes AR to limiting concentrations of androgen in prostate cancer cells possibly by increasing the apparent affinity of AR for ligand (Example 2) and through elevation of androgen-binding capacity (Example 3). The present invention provides a rational method for treating prostate cancers by inhibiting DDC, the method comprising administering to a subject one or several inhibitors of DDC. Whereas prior art would suggest that to prevent DDC from co-activating the AR, one would have to inhibit the interaction between DDC and the AR, the current invention is based on the novel and surprising finding that compounds which antagonize the enzymatic activity of DDC may be effective in the treatment or co-treatment of prostate cancer (Examples 6-10) and that the enzymatic products of DDC are not involved in this indirect activation of AR (Example 4). In brief, the findings in Examples 8-10 demonstrate that inhibiting DDC enzymatic activity with carbidopa in LNCaP and C4-2 (human prostate cancer cell lines) xenografts results in reduced PSA production and tumour growth rate. In brief, the findings in Example 8 demonstrate that inhibiting DDC enzymatic activity with carbidopa in LNCaP (human prostate cancer cell line) xenografts results in reduced PSA production and tumour growth rate. Therefore, a method is described that inhibits or antagonizes DDC enzymatic activity, as for example selected from the above mentioned group of DDC-e inhibitors.

In brief, the findings in Example 5 demonstrate that mutational analysis of the DDC pyridoxal phosphate (PLP) co-factor binding site (Lys303Ile), which results in loss of DDC catalytic activity, abrogates the AR-coactivation function of the enzyme. DDC co-activation of the AR is measured as increased AR-driven transcription. Residue 303 is the pyridoxal phosphate (PLP) co-factor binding site and necessary for DDC enzymatic activity. Furthermore, it is shown that mutation of residue 303 does not disrupt binding of DDC to the AR, that DDC co-activation of the AR is not dependent on the enzymatic products of DDC.

The sensitization of AR to low androgen concentrations should occur from a molecular mechanism that results in some increased efficiency of the receptor's ability to directly bind hormone. Using in vitro and cell line-based ligand-binding assays, we found an increase in the apparent affinity of AR for androgen by up to 2-fold (Example 2; FIG. 2) and an elevation of 66-71% in the maximum androgen-binding capacity ($B_{max}$) of the receptor, in the presence of DDC protein (Example 3; FIG. 3). Although with DDC overexpression, a higher apparent affinity for R1881 can contribute to the observed increase in $B_{max}$ for AR in cells, the elevation in androgen-binding capacity must ultimately result from an increase in the number of cytosolic AR molecules that are capable of binding ligand. Overall, these finds provide a possible mechanism by which DDC enhances androgen-dependent AR activity.

Figure 2A:
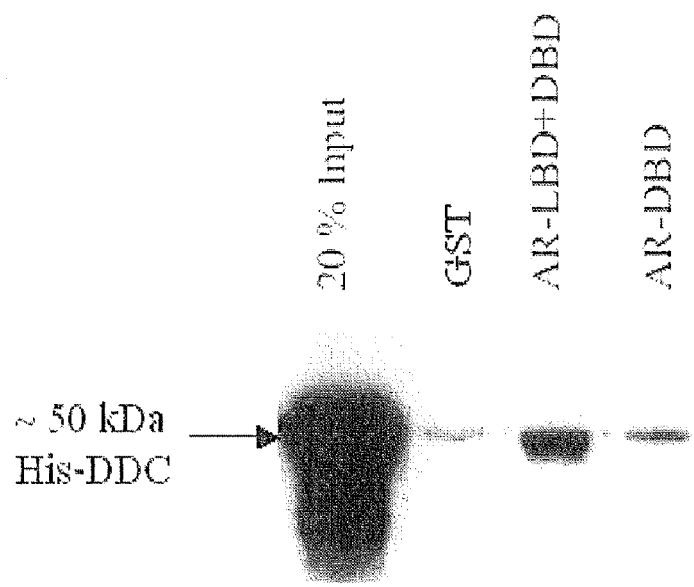
FIGS. 2A-B depict that purified His-DDC protein interacts with the AR-LBD and enhances apparent affinity of AR for androgen in vitro.

The observed increase in apparent affinity of the AR-LBD for androgen in the presence of purified His-DDC protein (Example 2; FIG. 2), suggests that DDC can actually modulate the mechanism by which ligand binds to the receptor. As this in vitro system only consists of AR-LBD, DDC and androgen, the increase in ligand-binding can be attributed to AR-LBD molecules binding R1881 more efficiently, with a higher proportion binding androgen, when an interaction occurs between DDC and the AR-LBD (Example 2; FIG. 2A). The effect of DDC on AR ligand-binding may involve intramolecular changes to the conformation of the AR-LBD. This could lead to structural alterations of the 11 α-helices that form the hydrophobic pocket of steroid receptors involved in recognition of cognate ligand, as well as positioning of helix 12 near the extreme C-terminus of the AR-LBD to expose the surface required for coactivator binding.

Figure 3A:
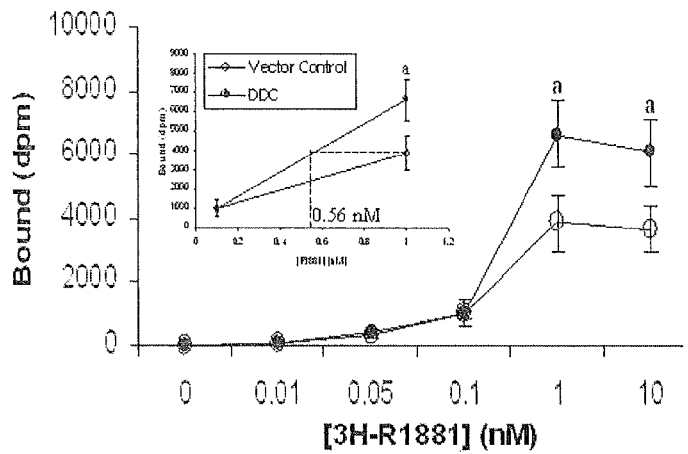
FIGS. 3A-C depict that DDC increases maximum androgen-binding capacity of AR in the cytosol and of nuclear androgen-bound AR of HeLa-AR cells, but does not increase cellular androgen-uptake in HeLa-AR Cells.
Figure 3B:
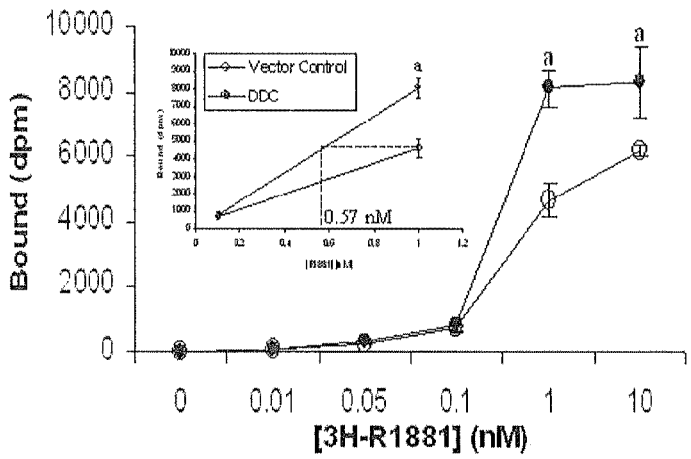

Overexpression of DDC in HeLa-AR cells confirmed that this coactivator can increase the apparent affinity of full-length AR for androgen in mammalian cells (Example 3; FIGS. 3A and 3B). In addition, with DDC overexpression, there is a significant increase in the total amount of bound-androgen, under saturation conditions (1-10 nM R1881), suggesting that a sub-population of AR molecules are not bound to ligand and remain localized to the cytoplasm even at high R1881 concentrations. These inactive AR molecules can be targeted by cytoplasmic coactivators, such as DDC, and by steroid receptor chaperone proteins. The interaction of DDC with AR can lead to a higher proportion of AR molecules being activated. Therefore, in contrast to the coactivation mechanism of classical steroid receptor coactivators, such as SRC/p160 family members and CBP/p300, which facilitate AR transcription by histone modifications, chromatin remodelling, and bridging of the receptor to components of basal transcriptional machinery, DDC can enhance AR transactivation by increasing ligand-binding affinity and capacity of the receptor in the cytoplasm, resulting in higher nuclear levels of AR.

Figure 3C:
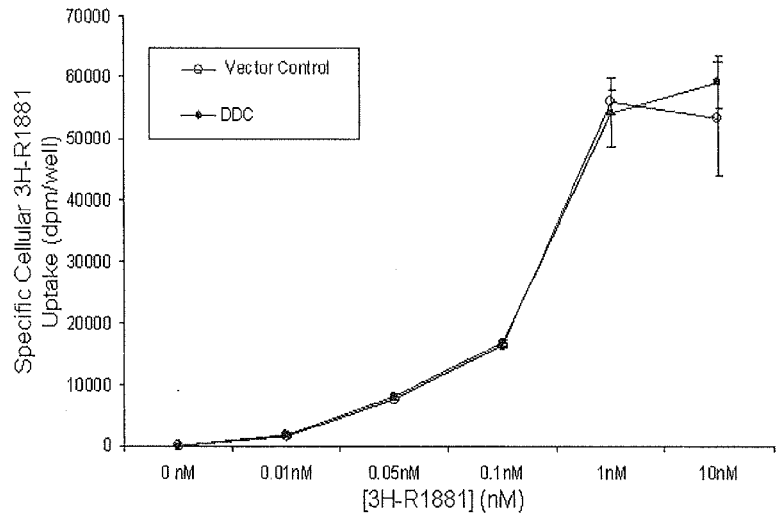

Since DDC is co-localized with AR only in the cytosol, one can speculate that the increased apparent affinity of AR for androgen, leading to elevation of AR maximum androgen-binding capacity ($B_{max}$) (Example 3; FIGS. 3A and 3B), is most likely associated with an increase in the on-rate of ligand-binding. Importantly, the lack of increased cellular androgen-uptake with DDC overexpression in HeLa-AR cells (Example 3; FIG. 3C), suggests that the increased $B_{max}$ of AR is due to a direct effect of DDC on the receptor in the cytosol and not via production of its neurotransmitter products or other unknown pathways. In other words, androgen uptake in the presence of DDC does not change, indicating that the increase in AR $B_{max}$ is not through synthesis of a DDC product that can alter the transcription or activity of other proteins that regulate androgen uptake and androgen binding to AR. Overall, the combination of in vitro purified protein and cell-based ligand-binding assays suggests that DDC can enhance AR transcriptional activity by increasing its androgen-binding capacity and apparent affinity for ligand, possibly through conformational changes in the ligand-binding domain of the receptor, prior to nuclear translocation.

Figure 7A:
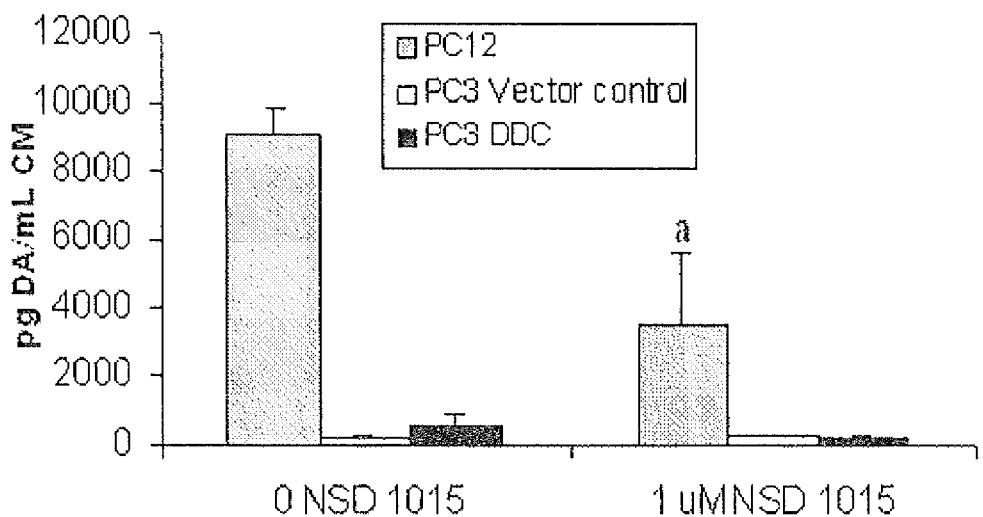
FIGS. 7A-B depict that DDC coactivation of AR transcription is independent of DA neurotransmitter using an ELISA for DA and using a transactivation assay.
Figure 7B:
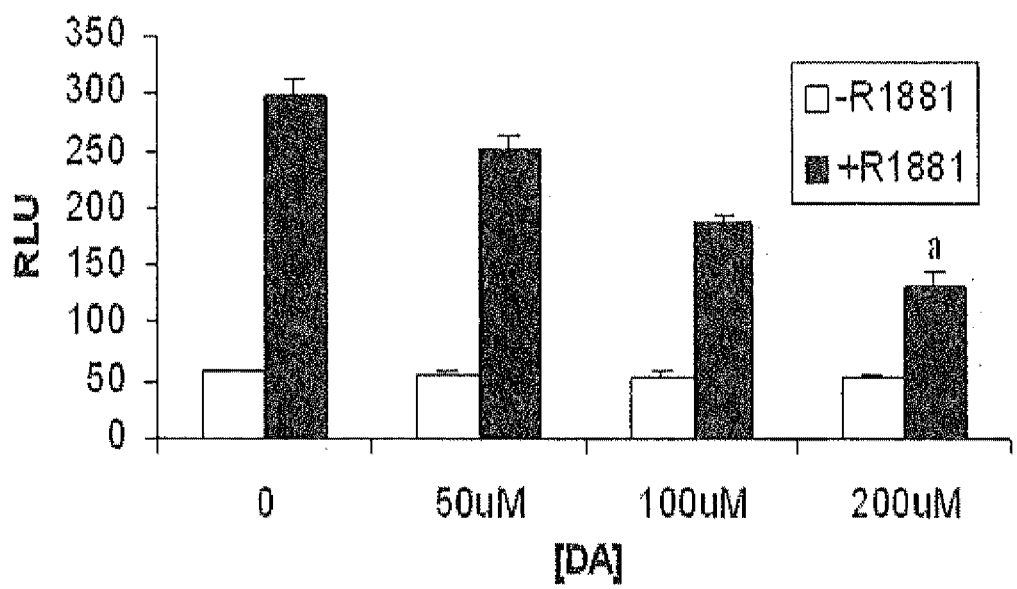
Figure 8A:
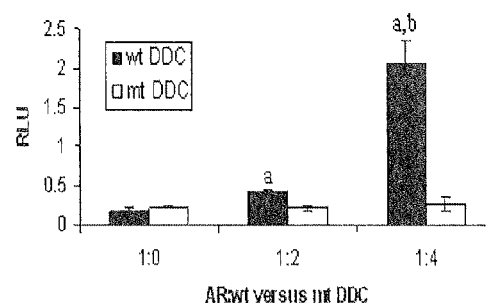
FIGS. 8A-D depicts that mtDDC does not coactivate AR transactivation in PC3 or LNCaP cells in the presence of androgen and that the expression level of mtDDC and wtDDC proteins were similar during the transactivation assay in PC3 and LNCaP cells.
Figure 8B:
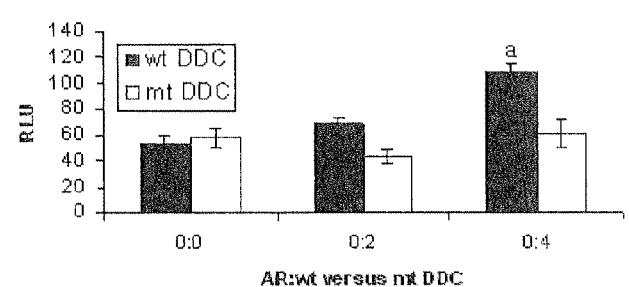

Although enzymatic products of DDC (DA and 5-HT) are not involved in the indirect activation of AR in prostate cancer cells (Example 4; FIGS. 6 and 7), mutational analysis of the PLP cofactor binding site (Lys303Ile) revealed that decarboxylation activity is necessary for enhancement of AR transcription (Example 5; FIGS. 8A and 8B). Replacing residue 303 of DDC with amino acids that are structurally distinct or even those that more closely resemble Lys results in dramatic loss of enzymatic activity, indicating that the shape and chemical properties of this residue are essential for catalysis. The lack of DA/5-HT involvement in the activation of AR and loss of coactivation function for enzymatically inactive mt DDC, suggest that this enzyme may be acting upon the receptor itself via the free α-COOH group of the AR terminal Gln919 residue or possibly upon another unknown protein or factor which may be required by DDC for its potential catalytic activity on AR. However, due to the high level of specificity of PLP-dependent enzymes for α-carbons of free amino acids, it is unlikely that DDC can utilize proteins as substrate. Alternative explanations are that the PLP cofactor of DDC also plays an important role in the formation of the active homodimer enzyme and hence, the inability of mt DDC to bind PLP can also prevent dimerization of DDC, which may be necessary for its enhancement of AR activity.

Figure 9:
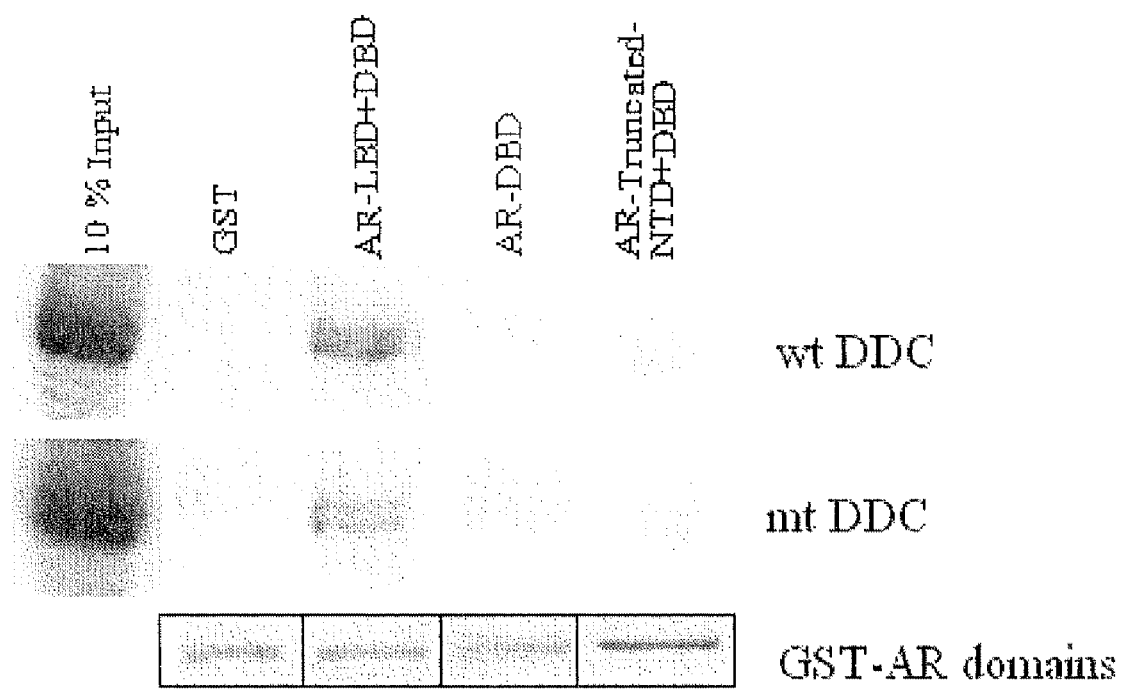
FIG. 9 depicts that the interaction of DDC with AR is independent of its enzymatic activity.

The Lys303Ile mt DDC bound to AR-domains in the same manner as wt enzyme (Example 5; FIG. 9), suggesting that the lack of an effect by mt DDC on activation of AR transcription is not a result of altered interaction with the AR. This interaction was the strongest with the LDB.

Figure 4A:
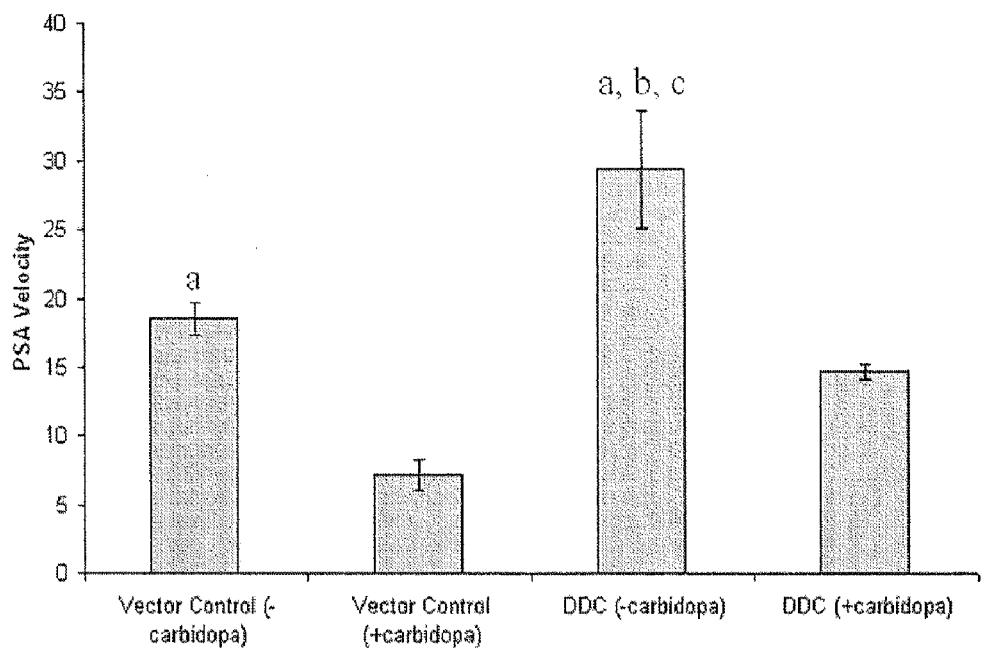
FIGS. 4A-B depict that carbidopa treatment reduces serum PSA levels and reduced xenograft tumour growth in LNCaP-DDC and LNCaP-Vector control xenografts.
Figure 4B:
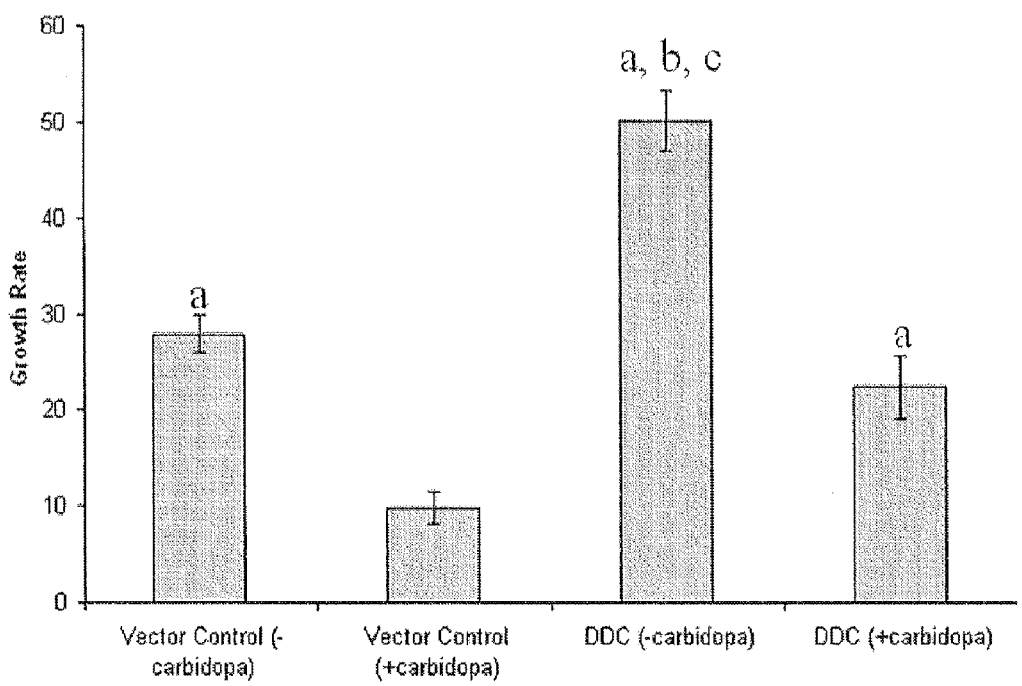
Figure 5:
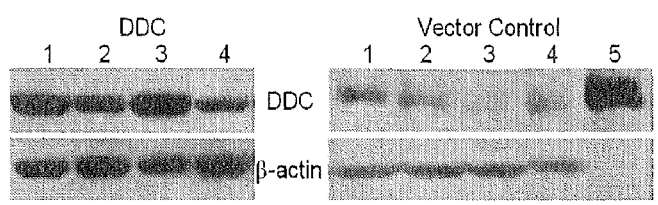
FIG. 5 depicts that endogenous and induced DDC levels exist in LNCaP-Vector control and LNCaP-DDC xenografts in the presence and absence of carbidopa.

The enhancement of AR transactivation by DDC was also confirmed in animal studies. Increased PSA production with DDC overexpression was seen in LNCaP xenografts, demonstrating that DDC can act as an AR coactivator in vivo (Example 8; FIG. 4A). There was observed a significant increase in tumour growth rate with overexpression of DDC (Example 8; FIG. 4B), suggesting that its coactivation function may lead to sustained AR activity and tumour growth. Importantly, when mice bearing LNCaP tumours that overexpressed DDC were treated with the DDC-specific enzymatic inhibitor, carbidopa, both PSA production (Example 8; FIG. 4A) and tumour growth rate (Example 8; FIG. 4B) were substantially decreased, demonstrating that inhibition of DDC catalytic activity is a viable means of treating prostate tumours. Notably, PSA production and tumour growth rate were reduced by carbidopa even when DDC was not overexpressed, indicating that the low levels of endogenous DDC expression and activity is important for LNCaP tumour growth (LNCaP-Vector control group of Example 8; FIGS. 4 and 5). In vitro growth assays confirmed that inhibition of endogenous DDC enzymatic activity with carbidopa, as well as with NSD-1015, in LNCaP cells inhibits the growth rate of these androgen-dependent prostate cancer cells (Example 6; FIG. 10). Similar treatment of the C4-2 androgen-independent prostate tumour cell line with carbidopa and NSD-1015 also resulted in a significant decrease in cell growth (Example 7; FIG. 11). Importantly, use of carbidopa to treat castrated mice bearing parental LNCaP tumours caused a substantial delay in progression to the androgen-independent phase of this xenograft model (Example 9; FIG. 12). Moreover, carbidopa treatment of C4-2 xenografts in pre-castrated mice significantly reduced the growth rate and PSA production of these tumours, which mimic castration-resistant clinical prostate cancers (Example 10; FIG. 13). Hence, in patients undergoing androgen-withdrawal therapy, DDC may serve to activate AR in the presence of limited concentrations of hormone, a process that can be blocked with the use of DDC enzymatic inhibitors. Provided in the current invention is a method that uses any type of DDC inhibitor in combination with other medication or intervention to treat all types of prostate cancers, including but not limited to androgen depletion therapy.

The extent of NE differentiation in prostate tumours, associated with more aggressive disease, increases upon hormone ablation therapy. We suggest that DDC may be important for the trans-differentiation process of AR-expressing luminal epithelial-derived adenocarcinoma cells into the NE-phenotype, and propose a model to explain how the coactivation function of DDC on AR can influence NE trans-differentiation of prostate tumours subjected to androgen ablation (sketched out in FIG. 14).

In the early stages of prostate cancer, AR exhibits robust activity and is susceptible to hormone ablation therapy. However, this treatment can induce the trans-differentiation of a population of luminal epithelial-derived adenocarcinoma cells into the NE-phenotype, which is characterized by increased expression of DDC and other NE markers. The resulting intermediate NE trans-differentiated cell can possess both luminal and NE characteristics, providing the environment in which DDC can coactivate AR. Prolonged hormonal therapy may lead to complete loss of AR activity/expression in some NE-phenotype cells and result in extremely high levels of DDC expression. These AR-independent NE cells can maintain their own growth through production of mitogenic factors and are resistant to hormone ablation treatment.

Figure 14:
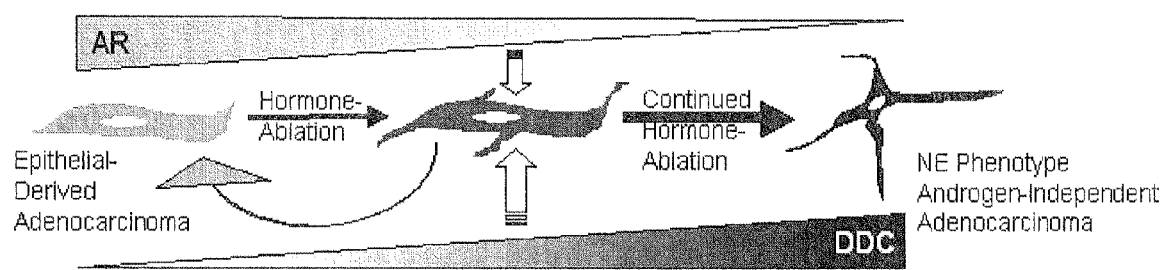
FIG. 14 depicts the role of DDC-AR coactivation in neuroendocrine trans-differentiation of prostate cancer adenocarcinoma cells.

Androgen withdrawal therapy temporarily reduces AR transcriptional activity, which induces the NE-phenotype characterized by high-level expression of NE markers such as DDC. The expediency of NE characteristic accumulation may vary among adenocarcinoma cells depending on exposure to other differentiating factors within their microenvironments. During NE trans-differentiation, intrinsic AR activity is minimal but DDC and other coactivators can interact with and sensitize the receptor to limiting levels of androgen, leading back to more AR-dependent tumour cell growth. This process of trans-differentiation and de-differentiation may continue during the entire course of treatment as the patient succumbs to disease. It is also possible that sustained and extensive hormonal therapy may lead to total loss of AR expression/function, resulting in a completely NE cancer (FIG. 14). Pure NE cell tumours of the prostate are rare but extremely aggressive. At this stage, adenocarcinoma cells are AR-independent and can maintain their own growth through secretion of mitogenic NE factors. Overall, transition to the NE-phenotype may be a mechanism adopted by androgen-dependent carcinoma cells to allow their survival under androgen-deprived conditions.

The necessity of DDC decarboxylation activity for enhancement of AR transactivation (Example 5; FIG. 8) provides an additional opportunity to target receptor function by simply utilizing existing clinically tested enzymatic inhibitors. Moreover, targeting DDC, at two different stages of disease, may provide a unique means of repressing AR function and cancer progression in patients that exhibit extensive multifocal NE differentiation. First, DDC coactivation function can be targeted during the AR-dependent NE trans-differentiation phase, which may include early-stage up to AI disease, depending on the patient, and secondly in rare cases of completely AR-independent disease. In the latter case, targeting DDC would inhibit synthesis of serotonin or other amino acid metabolic products that may act as mitogenic factors. The enzymatic inhibitor of DDC, carbidopa, has been recently used to treat mice bearing tumours from implanted prostate NE cancer cells derived from a NE-cell-transformed transgenic mouse model (Ippolito). In combination with other drugs, carbidopa resulted in a 40% reduction of tumour growth. We find that use of pure carbidopa to treat LNCaP (human prostate cancer cell line) tumour xenografts in non-castrated mice results in significant reduction of PSA production (velocity) and tumour growth rate (Example 8; FIG. 4), demonstrating that use of carbidopa alone is sufficient to treat prostate tumours. In addition, we demonstrated that carbidopa treatment of castrated mice bearing LNCaP tumours substantially delays progression to androgen-independence (Example 9; FIG. 12) and reduces PSA velocity/tumour growth rate of androgen-independent C4-2 tumours that represent hormone refractory clinical prostate cancers (Example 10; FIG. 13). It is possible that patients diagnosed as having highly NE-differentiated tumours, which is correlated with development of more aggressive cancer, can be given more aggressive therapy that includes inhibitors targeting enzymatic activity of DDC. As part of the present invention, methods are provided comprising administration of compounds that may be directed towards certain types or stages of prostate cancer, including but not limited to tumours that show signs of NE-differentiation and AI.

EXAMPLES

The following examples are presented to illustrate the present invention and to assist one of ordinary skill in making and using the same. The methodology and results may vary depending on the intended goal of treatment and the procedures employed. The examples are not intended in any way to otherwise limit the scope of the invention.

Example 1

DDC Enhances AR Transactivation from the Androgen-Regulated PSA Promoter and Sensitizes the Receptor to Limiting Androgen Concentrations Description of Study Procedures
Plasmid Construction The DDC expression plasmid, pDEST12.2-DDC, used for mammalian cells and for in vitro transcription/translation was cloned previously. Full-length human AR was cloned into the pcDNA3.1 mammalian expression plasmid (pcDNA3.1-hAR) under control of a cytomegalovirus (CMV) promoter.
Transactivation Assays PC3 and LNCaP cells were transfected, treated with R1881 and used for luciferase assays, as described previously. Briefly, human AR expression plasmid (pcDNA3.1-hAR) and AR-regulated luciferase reporters, pARR3-tk-Luc or pPSA-630 bp-Luc (−630/+12 bp of the 5' PSA flanking region) {Snoek, 1998 #136}, were cotransfected into cells, along with DDC expression plasmid (pDEST12.2-DDC) or control empty vector (pDEST12.2). Firefly luciferase values were normalized to renilla luciferase (PRL-TK reporter; Promega Corp.) and expressed as relative luciferase units (RLU).
Results and Interpretation In AR transfected PC3 cells overexpressing DDC (1:4 ratio of human AR:DDC) and treated with 1 nM R1881, AR transactivation for the proximal PSA and ARR3-tk promoters were increased 2.5-fold and 9-fold, respectively (FIG. 1A). Due to the stronger enhancement of AR transactivation seen with the ARR3-tk promoter, this reporter was used to determine the effects of DDC overexpression on AR activity under limiting androgen conditions in androgen-independent and -sensitive prostate cancer cell lines. PC3 cells, transfected with AR, and LNCaP cells that express endogenous AR were used to measure receptor transactivation at varying concentrations of R1881. In both PC3 and LNCaP cells, activation of AR transcription required a minimum concentration of 0.1 nM R1881. Overexpression of DDC enhanced AR activity by 2.5-fold in LNCaP cells and approximately 5.5-fold in PC3 cells (FIGS. 1B and 1C) at this threshold androgen concentration. At higher R1881 levels of 1 nM and 10 nM, we observed the usual high 8-fold (1 nM) and 6-fold (10 nM) increases in AR transactivation for PC3 cells and a 2-fold increase for LNCaP cells. The substantial enhancement of AR transcription seen with DDC overexpression at 0.1 nM R1881 demonstrates that this coactivator can render AR more responsive to low concentrations of androgen.

Example 2

DDC Increases the Apparent Affinity of AR for Androgen In Vitro

Description of Study Procedures
Plasmid Construction

The His-tagged-DDC bacterial expression plasmid was produced via RT-PCR on LNCaP RNA and Gateway™ cloning (Invitrogen). The forward (5'GGGGACAAGTTTGTA-CAAAAAAGCAGGCTTAAACGCAAGTGAATTCC GAAGGAGA-3') SEQ ID NO. 1 and reverse (5'GGGGAC-CACTTTGTACAAGAAAGCTGGGTCCTACTCCCTCT CTGCTCG CAGCAC-3') SEQ ID NO. 2 primers contained a stop codon, but lacked the ATG start site to allow for a 6×-His-tagged-DDC N-terminal fusion. Primers also included DDC gene-specific coding sequence (in bold) and attB1/B2 recombination sites allowing incorporation of the PCR product into pDONR201 for generation of the pENTR-fusion-DDC vector. Upon frame and sequence verification, this entry vector was used for a recombination reaction with pDEST17 to produce the pDEST17-His-DDC bacterial expression plasmid (T7 promoter).

Mammalian Cell Culture

PC12 rat adrenal pheochromocytoma cells were grown in DMEM media containing 5% FBS and 10% horse serum (GibcoBRL).

In Vitro Ligand Binding Assays

Recombinant rat thioredoxin-fused AR ligand binding domain (PanVera, 1.390 mg/mL, 48.4 kDa), which is identical to the human AR-LBD, was used for hydroxylapatite (HAP) pulldown ligand binding assays at R1881 concentrations of 0 to 1000 nM {Portigal, 2002 #86}. Initially, his-tagged-DDC protein was expressed in BL21-SI bacteria, containing the pDEST17-His-DDC plasmid, and purified using a nickel-nitrilotriacetic acid (Ni-NTA)-agarose column according to the manufacturer's protocol (Qiagen). Purified AR-LBD was diluted to a final concentration of 1 µg/mL in binding buffer (50 mM Tris pH 7.5, 10% glycerol, 0.8 M NaCl, 1 mg/mL BSA and 2 mM dithiothreitol), containing tracer 20 nM [$^3$H]-R1881 (NEN Life Science Products, 75.2 Ci/mmol, 1 mCi/mL). In order to minimize the use of radioactive ligand, supplemental cold R1881 was added to the assay mix to achieve the high 100 nM and 1000 nM total R1881 concentrations. Assays were carried out in the absence and presence of 0.5 µg of His-DDC protein, which was added directly to the 1 mL assay mix. Following overnight incubation at 4° C., a 50% HAP slurry (Calbiochem Fast Flow hydroxylapatite in 10 nM Tris pH 8.0 and 1 mM EDTA) was added to the assay, pellets were incubated on ice for 10 minutes, and then washed four times with wash buffer (40 mM Tris pH 7.5, 100 mM KCl, 1 mM EDTA and 1 mM EGTA). HAP pellets were resuspended in ethanol and bound [$^3$H]-R1881 was measured (disintegrations per minute, dpm) using a Beckman LS 6500 scintillation counter.

To determine non-specific binding (NSB) to the HAP matrix, control pulldown assays were carried out using an assay mix that lacked AR-LBD. In addition, to assess His-DDC non-specific binding to the HAP matrix and R1881, pulldown assays were performed with 0.5 µg of His-DDC protein, in the absence of AR-LBD (NSB due to His-DDC protein was minimal; 90% of NSB was due to HAP matrix). NSB values were subtracted from sample measurements for determination of specific binding. The total dpm per assay was determined by measuring a known amount of [$^3$H]-R1881 and normalizing to the total assay volume (1 mL). All assays were carried out in triplicate and the pmole bound [$^3$H]-R1881/mg AR-LBD protein was calculated by using the measured dpm of tracer 20 nM [$^3$H]-R1881. Calculated values were then extrapolated to determine total ligand bound at the 10 nM, 100 nM and 1000 nM R1881 concentrations. Results were expressed as the mean total pmole bound R1881/mg AR-LBD protein (±SEM).

GST-Pulldown Assays

GST-pulldown assays were also carried out with the purified His-DDC protein (0.5 µg/assay) used for in vitro ligand binding assays. His-DDC protein was incubated with GST-AR domains as done for radiolabeled proteins (Example 5) and bound protein was detected via Western blot analysis.

Results and Interpretation

Figure 2B:
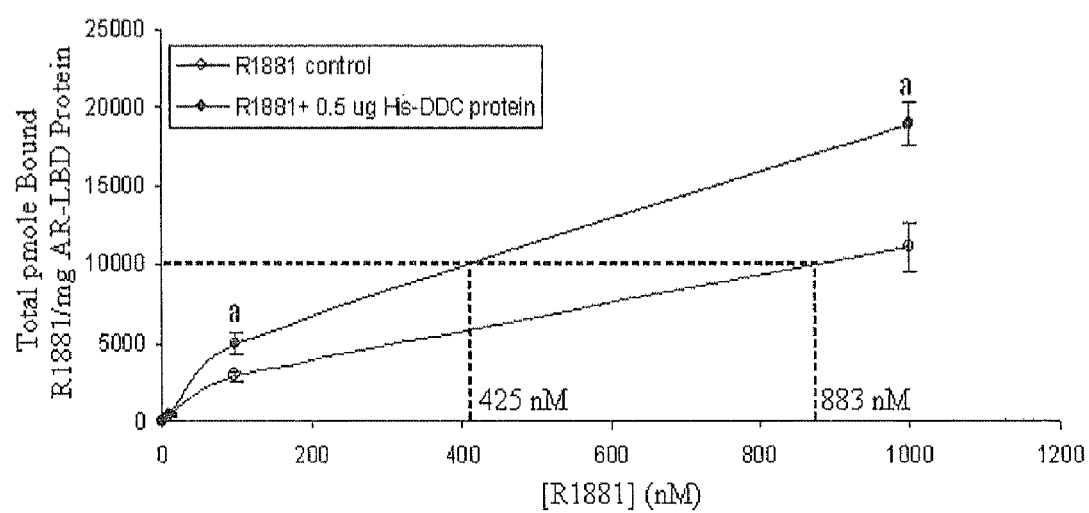

We next tested the ability of DDC to influence AR androgen-binding ability, using purified AR-LBD and His-tagged-DDC protein. Nickel NTA-affinity purified His-DDC was analyzed using SDS-PAGE/Coomassie Blue staining and detected at the known molecular weight of ~50 kDa with negligible degradation (data not shown). Initial testing for AR-binding activity, using GST-pulldown and Western blot analysis, revealed that His-DDC protein binds strongly to the AR-LBD, while its interaction with the DBD is minimal (FIG. 2A). Subsequent, in vitro ligand binding assays (0-1000 nM R1881) demonstrated that in the absence of His-DDC, an R1881 concentration of 883 nM was required to 50% saturate total AR-LBD protein, while in the presence of His-DDC a lower androgen amount of 425 nM was necessary to reach the same level of saturation. This corresponds to a 2.1-fold higher apparent affinity for androgen by the AR-LBD, when His-DDC is present (FIG. 2B). Non-specific binding of ligand to His-DDC protein interacting with the AR-LBD was negligible at the tracer concentration of 20 nM [$^3$H]-R1881 (AR-LBD control=895±93 versus AR-LBD+His-DDC=937±111 pmole bound R1881/mg AR-LBD).

Although incubation of His-DDC with AR-LBD protein resulted in a 1.75-fold (75%) and 1.71-fold (71%) respective increase in bound R1881 at the 100 nM and 1000 nM concentrations, the lack of AR-LBD protein total saturation prevented determination of a maximum androgen binding capacity ($B_{max}$). However, since a known amount of AR-LBD protein and R1881 was used for each assay, the efficiency of androgen-binding was determinable. In the absence and presence of His-DDC protein, only about 5% of all available ligand remained bound to the pulled down AR-LBD at the tracer concentration of 20 nM [$^3$H]-R1881. In the absence of DDC, higher R1881 concentrations of 100 nM and 1000 nM increased ligand-binding efficiency to 14% and 54%, respectively. The total amount of available ligand that bound to the AR-LBD increased to 24.5% (100 nM) and 92% (1000 nM) upon addition of His-DDC protein. Overall, these results suggest that direct association of DDC with the ligand-binding domain of AR can increase its apparent affinity for androgen, leading to higher ligand-binding efficiency for the receptor.

Example 3

DDC Elevates AR Androgen-Binding Capacity in Mammalian

Cells

Description of Study Procedures

Cell-Based Ligand Binding Assays

HeLa-AR cells were cultured for 24-48 hours in DMEM containing 5% DCC-FBS and seeded onto 6 cm plates at a density of 1×10$^6$ cells/plate. After 5 hours, cells were transfected with either pDEST12.2-DDC or pDEST12.2 control vector (5 µg/plate) using Lipofectin Reagent (Invitrogen). The next day, transfection mix was changed to DMEM supplemented with 5% DCC-FBS containing increasing concentrations of [$^3$H]-R1881 (0-10 nM). To determine non-specific binding, hormone treatments were carried out in the presence (NSB) and absence (total binding) of excess cold 1000 nM R1881. After 24 hours of incubation with hormone, cells were harvested as described previously. Cytosolic fractions were prepared by resuspending cell pellets in Buffer A (10 mM HEPES pH 7.9, 10 mM KCl, 0.1 mM EDTA, 0.1 mM EGTA, 1 mM dithiothreitol/DTT, 0.5 mM phenylmethylsulfonyl fluoride/PMSF) and incubating on ice for 15 minutes. After addition of NP-40, the cell suspension was vortexed, centrifuged and supernatant cytosolic fractions were stored at −80° C. Nuclear pellets were resuspended in Buffer C (20 mM HEPES pH 7.9, 0.4 M NaCl, 1 mM EDTA, 1 mM EGTA, 1 mM DTT, 1 mM PMSF) and samples were vigorously rocked for 15 minutes on a shaking platform {Schreiber, 1989 #139}. Nuclear extracts were centrifuged and supernatants were frozen at −80° C.

Cytosolic and nuclear extracts were then thawed and incubated for 6 hours with agarose beads conjugated to FLAG monoclonal antibody (Sigma, USA). Lysate aliquots (10%) were also used for SDS-PAGE/Western blot analysis, with an anti-AR441 mouse monoclonal antibody (Santa Cruz Biotechnology) to determine the expression level of FLAG-tagged AR protein, as described previously. Beads were washed with Buffer D (20 mM HEPES pH 7.9, 20% glycerol, 0.3 M KCl, 0.2 mM EDTA, 0.05% NP-40, 0.5 mM DTT, 0.5 mM PMSF) and specifically bound ligand (total binding—NSB) to the immunopreciptated FLAG-tagged AR protein was determined by measuring the levels of tritium (dpm) in bead resuspensions using a scintillation counter. All measured bound dpm values were normalized to corresponding Western blot AR protein band intensities. Results were expressed as the relative (normalized to the level of AR protein) mean bound ligand of three replicates (±SEM).

For cellular ligand-uptake assays, HeLa-AR cells were seeded onto 6-well plates at a density of $3 \times 10^5$ cells/well and transfected using either pDEST12.2-DDC or pDEST12.2 control vector (1 µg/well), as done above for cell-based ligand binding assays. Cells were then incubated with increasing concentrations of [$^3$H]-R1881 (0-10 nM) for 24 hours. Non-specific cellular androgen uptake was determined by incubating with excess cold 1000 nM R1881. Cells were washed, harvested by scraping and lysed using RIPA buffer (50 mM Tris-Cl pH 7.5, 150 mM NaCl, 1% NP-40, 0.5% sodium deoxycholate, 0.1% SDS). Whole cell extracts were used for scintillation counting to determine cellular [$^3$H]-R1881 accumulation. Results were expressed as the mean specific cellular [$^3$H]-R1881 uptake (total uptake−non-specific uptake) of three replicates (±SEM).

Results and Interpretation

The effect of DDC overexpression on AR androgen-binding capacity was tested in HeLa-AR cells, which express high levels of FLAG-tagged wild-type human AR that can be consistently isolated. HeLa-AR cells, transfected with a DDC expression plasmid or vector control, were treated with increasing concentrations of [$^3$H]-R1881 (0-10 nM) and the amount of androgen bound to immunprecipitated AR in cytosolic and nuclear fractions was determined. Specifically bound-androgen values were normalized to the level of AR protein to account for variations in receptor protein stability due to [$^3$H]-R1881. Notably, AR was still present in the cytosol at the 1 nM and 10 nM R1881 concentrations, suggesting that in HeLa-AR cells not all receptor molecules bind ligand even at high androgen levels.

For immunoprecipitated AR from the cytosol, DDC overexpression resulted in a 1.71-fold (71%) and 1.66-fold (66%) increase in the maximum androgen binding capacity at the 1 nM and 10 nM saturation concentrations of [$^3$H]-R1881, respectively (FIG. 3A). A significant increase in $B_{max}$ was also detected in nuclear fractions in the presence of DDC at the 1 nM and 10 nM ligand concentrations, presumably due to increased cytosolic androgen-binding and translocation of AR to the nucleus (FIG. 3B). In addition, similar to the in vitro AR-LBD ligand binding assay (FIG. 2B), we observed a 1.79-fold increase in the apparent affinity of AR for androgen when DDC was overexpressed in the cytosol (FIG. 3A). This effect was observed in the 0.1 nM to 1 nM R1881 concentration range where minimal to 100% saturation occurred, respectively. In the presence of DDC a significantly lower amount of R1881 (0.56 nM) was required to reach the control $B_{max}$, which occurred at 1 nM R1881. Since it is possible that DDC overexpression in HeLa-AR cells may indirectly modulate transport of ligand, cellular androgen-uptake assays were performed at varying concentrations of [$^3$H]-R1881. The specific cellular-uptake of androgen did not change with DDC overexpression (FIG. 3C). Taken together, these data suggest that overexpression of DDC in the cytosol can increase the affinity of AR for androgen and possibly increase the population of AR molecules that can bind ligand, resulting in the observed higher $B_{max}$ for the receptor.

Example 4

DDC Enhancement of AR Transactivation is Independent of its Neurotransmitter Products Description of Study Procedures Some of the study procedures used in this example has been described in the previous examples.

Mammalian Cell Culture

PC12 rat adrenal pheochromocytoma cells were grown in DMEM media containing 5% FBS and 10% horse serum (GibcoBRL).

cAMP Assays

PC3 and LNCaP cells were seeded in 12-well plates at a density of $1.5 \times 10^5$ cells/well. The next day, cells were gently washed three times with serum-free media to remove excess FBS and grown for a further 24 hours in the absence of serum. Cells were then stimulated with various concentrations of DA for 15 minutes or 5-HT for 10 minutes at 37° C. Cells were lysed and intracellular cAMP levels were determined using the cAMP Biotrak Enzymeimmunoassay System (Amersham Biosciences) following the manufacturer's instructions. Assays were performed in triplicate with two independent trials.

Transactivation Assays

Transactivation assays for AR were also performed in PC3 cells treated with dopamine (DA) and serotonin (5-HT, 5-hyroxytyrptamine), which were purchased from Sigma. As described above, cells were transfected with pcDNA3.1-hAR, pRL-TK-renilla and pARR3-tk-Luc reporter but DDC was excluded. Cells were then treated with or without 1 nM R1881 and varying concentrations of pure DA or 5-HT in 5% dextran-coated charcoal stripped FBS (DCC-FBS) for 24 hours before harvest and luciferase assay.

Dopamine ELISAs

PC3 cells were seeded in 12-well plates at a density of $1.5 \times 10^5$ cells/well and transfected the following day with pcDNA3.1-AR and pDEST12.2-DDC or pDEST12.2 empty vector control, as described above for transactivation assays. The next day, media was changed to 5% DCC-FBS containing 1 nM R1881. Conditioned culture media was removed 24 hours later and stored at −80° C. A 100 µL volume of media was used for the competitive enzyme-linked immunosorbent assay (ELISA). Dopamine was assayed using the Dopamine Research Enzyme Immunoassay kit (Rocky Mountain Diagnostics) following the manufacturer's instructions. PC12 cells, used as a positive control, were grown to 70% confluency (12-well plates) and conditioned media was collected 24 hours later for assay, as above. Secreted DA levels from PC3 and PC12 cells were determined in the presence and absence of 1 µM NSD-1015 (3-hydroxybenzylhydrazine) DDC enzymatic inhibitor (Sigma). All ELISAs were performed in triplicate with two independent trials.

Results and Interpretation

Figure 6A:
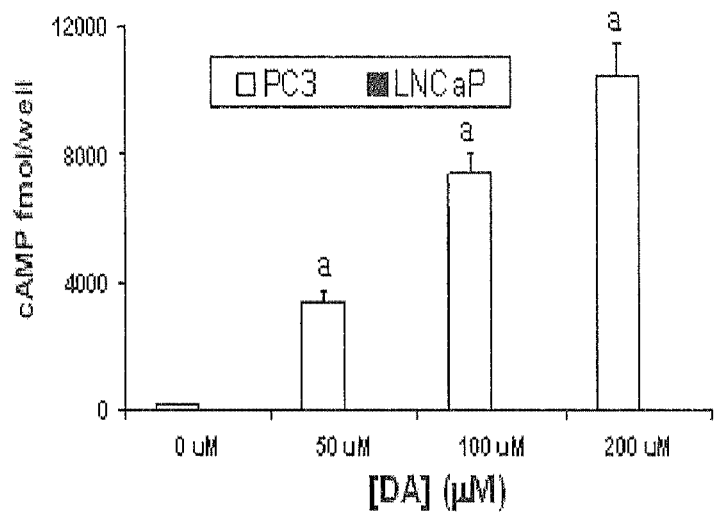
FIGS. 6A-B depict the effect of DA and 5-HT on Induction of Intracellular cAMP Levels in PC3 and LNCaP Cells.
Figure 6B:
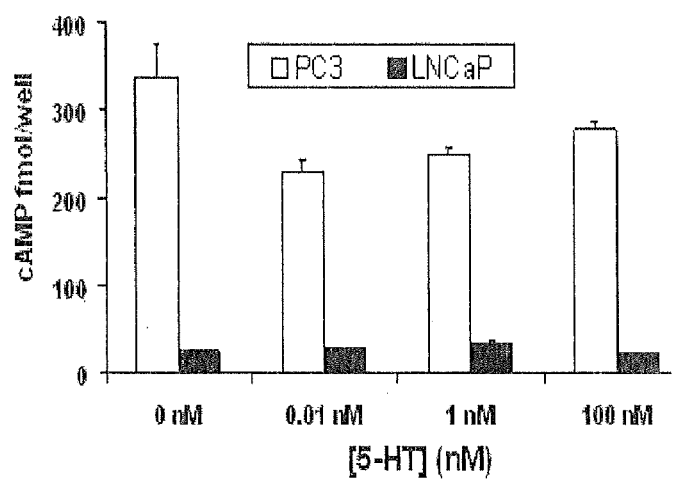

Prior to determining whether DDC enzymatic products, DA and 5-HT, are involved in the activation of AR, initial detection of their cell surface GPCRs was carried out in PC3 and LNCaP cells using cAMP assays. In PC3 cells, DA stimulated a dose-dependent increase in intracellular cAMP to levels that were ~52-fold higher than untreated cells, at the maximum 200 µM concentration (FIG. 6A). In LNCaP cells, DA did not induce a significant cAMP response at all concentrations. Similarly, 5-HT treatment did not increase cAMP levels in either prostate cancer cell line (FIG. 6B). These data suggest that functional and robust DA D1-like (cAMP elevating) GPCRs are present in PC3 cells and that 5-HT receptors do not induce cAMP-mediated signalling pathways in PC3 or LNCaP cells, although both cell lines have been shown to express 5-HT GPCRs {Abdul, 1994 #63; Abdul, 1995 #64; Dizeyi, 2004 #65; Siddiqui, 2006 #62; Jongsma, 2000 #66}.

Since the most profound coactivation effect of DDC on AR occurs in PC3 cells (8-9 fold compared to 2-fold in LNCaP cells, FIG. 1) that contain functional DA receptors, ELISAs for DA were carried out using conditioned medium (CM) from PC3 cells overexpressing DDC to determine whether DA is produced under transactivation assay conditions. PC12 rat adrenal pheochromocytoma cells, known to express high levels of active DDC enzyme that produces DA, were used for comparison. ELISAs were performed in the absence and presence of a DDC inhibitor, NSD-1015, to demonstrate that DA production is due to direct activity of the enzyme (FIG. 7A). With DDC overexpression in PC3 cells, extremely low levels of secreted DA were observed (522±431 pg/mL CM) as compared to the PC12 positive control cell line (9106±688 pg/mL CM). Addition of NSD-1015 reduced DA production to basal levels in DDC overexpressing PC3 cells (220±85 pg/mL CM), while reducing PC12 DA levels by 2.6-fold (3561±2032 pg/mL CM). cAMP assays were then used to determine whether the almost negligible levels of DA produced with DDC overexpression could activate the robust DA receptors in PC3 cells. Elevation of intracellular cAMP levels could not be detected in PC3 cells that overexpressed DDC to the same extent as in DA ELISAs (data not shown) suggesting that activation of DA GPCRs does not occur under transactivation assay conditions.

Nevertheless, in order to determine the direct potential effects of DA and 5-HT on AR transcriptional activity, AR transfected PC3 cells were treated with the neurotransmitters in transactivation assays. DA treatment resulted in a reduction of ligand-dependent AR transcription, with a 2.2-fold repression at the highest 200 µM concentration (FIG. 7B). Ligand-independent activation of AR was not affected by DA, indicating that its effect on AR activity is not due to a general cytotoxic effect on PC3 cells. In contrast, 5-HT treatment of PC3 cells (0-100 nM) did not alter AR activity in the absence or presence of ligand. Taken together, the combination of the above data strongly suggest that DA and 5-HT production and autocrine activation of their GPCRs are not responsible for the enhancement of AR activity observed with DDC overexpression in PC3 and LNCaP cells.

Example 5

DDC Enhancement of AR Transactivation is Dependent on its Enzymatic Activity

Description of Study Procedures

Some of the study procedures used in this example have been described in the previous examples.

Generation of Mutant DDC

The QuikChange™ Site-Directed Mutagenesis kit was used to introduce a single nucleotide mutation in the PLP cofactor binding site of DDC that converted Lys303 into Ile. PCR-based mutagenesis was performed on the pENTR-DDC vector using forward (5'-ATTCAACTTTAATCCCCACA TATGGCTATTGGTGAATTTTG-3') SEQ ID NO. 3 and reverse (5'-CAAAATTCACCAATAGCCATATGTGG GGATTAAAGTTGAAT-3') SEQ ID NO. 4 primers that replaced the AAA (Lys303) codon with ATA (Ile303). After sequence verification, the mutated pENTR-DDC vector was used for an LR recombination reaction with pDEST12.2 (Gateway™ Technology, Invitrogen) to produce the pDEST12.2-mt-DDC vector (utilized for Transactivation and GST-pulldown assays).

GST-Pulldown Assays

GST protein and three rat GST-AR domain fusion proteins ($AR_{234-665}$/Truncated-NTD+LBD, $AR_{541-665}$/DBD, $AR_{541-919}$/DBD+LBD) were coupled to glutathione-agarose beads at equimolar levels. The pDEST12.2-DDC (wt DDC) and pDEST12.2-mt-DDC (mt DDC) vectors were used for in vitro transcription/translation with [$^{35}$S]-methionine. After incubation of radiolabeled proteins with GST-AR domains, bound protein was eluted for SDS-PAGE and autoradiography analysis.

Results and Interpretation

Figure 8C:
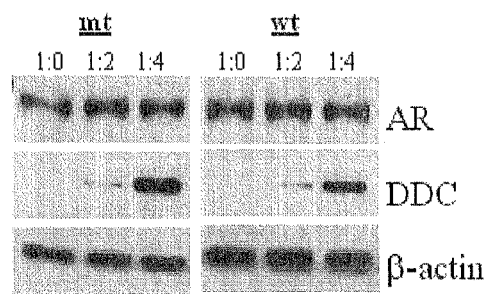
Figure 8D:
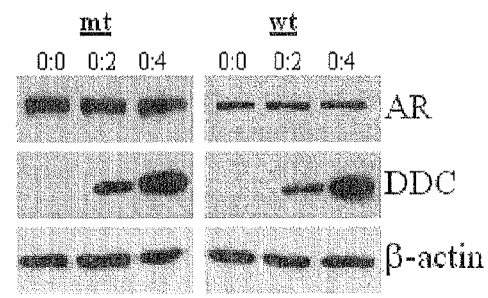

The necessity of DDC catalytic activity for enhancement of AR transcription was assessed by comparing AR transactivation assays for wild-type (wt) DDC and a mutant (mt) form of the enzyme, containing a Lys303Ile mutation in the PLP cofactor binding site. Maximal overexpression (1:4 ratio of AR:DDC) of wt DDC resulted in the usual approximate 10-fold and 2-fold increase of ligand-dependent AR transcription in PC3 and LNCaP cells, respectively (FIGS. 8A and 8B). However, the same level of mt DDC overexpression did not affect the magnitude of R1881-induced AR transactivation in PC3 or LNCaP cells, demonstrating that the single amino acid mutation of Lys303Ile completely abrogates DDC coactivation function. Notably, the lack of mt DDC coactivator activity is not due to lower expression or protein stability, as determined by Western blot analysis (FIGS. 8C and 8D). In contrast to the transactivation assays, the Lys303Ile mutation did not affect direct binding of DDC to AR in GST-pulldown assays (FIG. 9). The strongest interaction for wt and mt DDC protein occurred with the AR-LBD+DBD fragment as compared to the AR-truncated-NTD+DBD region. Since interaction with AR-DBD was almost negligible, binding of DDC with AR can be largely attributed to its affinity for the LBD of the receptor. Thus, these results demonstrate that the catalytic decarboxylase activity of DDC is necessary for its enhancement of AR transcription, but the single point mutation of Lys303 is not sufficient to significantly alter the in vitro conformation of the enzyme that mediates interaction with the receptor.

Example 6

DDC Inhibitors Decrease the Rate of Cell Growth of Androgen-Dependent LNCaP Cells In Vitro Description of Study Procedures Cell Proliferation Assay Cell proliferation assays were performed using the 3-(4,5-dimethylhiazol-2-yl)-5-(3-carboxymethoxyphenyl)-2-(4-sulfophenyl)-2H-tetrazolium Assay (MTS) according to the manufacturer's protocol, with minor modifications (Promega). LNCaP cells were plated in 96-well plates at a density of 3000 cells per well and incubated in RPMI medium containing 5% CSS for one day. On the following day, the DDC inhibitors, carbidopa (25 and 50 μM) and NSD-1015 (10 μM)±0.1 nM R1881 were added to each well in charcoal-stripped serum (CSS; Hyclone, VWR) RPMI media. The cells were harvested at days 0, 2, 4, 6 and 8, with a medium change every 3 days. Each time point was measured with 6 replicates.

Statistical Analysis

Student's t-test (two-sample equal variance) was used to evaluate statistically significant differences. All calculated p-values were two-sided and those less than 0.05 were considered statistically significant.

Results and Interpretation

Figure 10A:
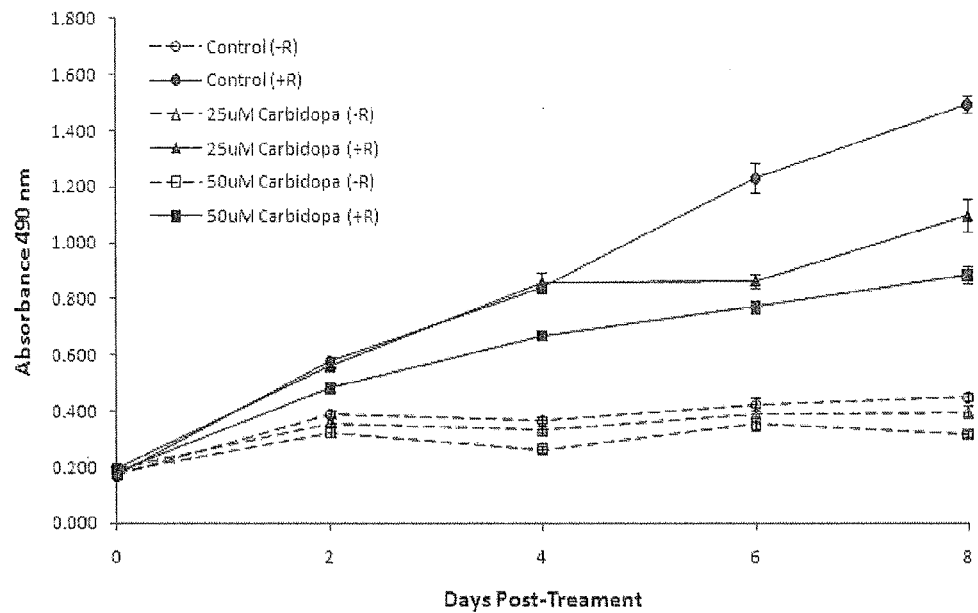
FIG. 10 shows the effects of DDC inhibitors on the growth of androgen-dependent LNCaP cells.
Figure 10B:
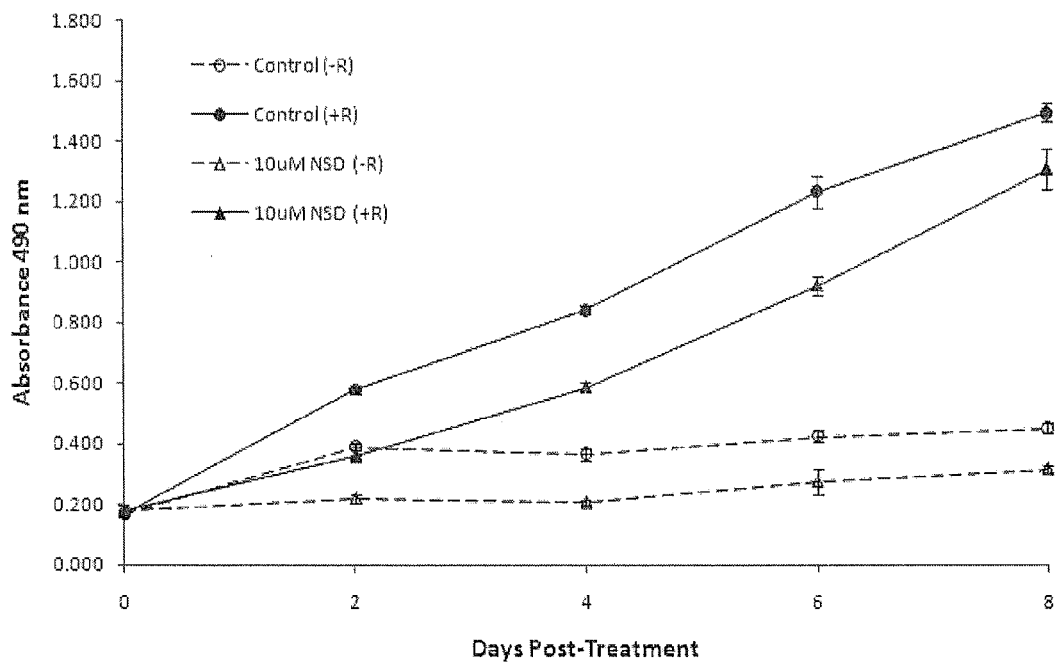

To determine whether inhibition of DDC enzymatic activity can affect the growth of prostate cancer cells in vitro, androgen-dependent LNCaP cells that express endogenous DDC and AR were treated with carbidopa and an additional inhibitor (NSD-1015) that is ideal for cell culture systems. Treatment of LNCaP cells with carbidopa resulted in a significant dose-dependent (25 μM and 50 μM) reduction of growth such that by day 8 and at the 50 μM concentration the number of cells were reduced by 1.42-fold in the absence of androgen and by 1.69-fold in the presence of androgen relative to the control non-treated cells (FIG. 10A). Treating LNCaP cells with NSD-1015 for 8 days (10 μM concentration), also caused a significant reduction in cell growth, with a 1.43-fold decrease in the absence of hormone and a 1.15-fold decline in the presence of hormone (FIG. 10B). The results are presented as mean±S.E. of 6 replicates. Taken together, these data indicate that inhibiting DDC catalytic activity with multiple inhibitors results in a considerable reduction of prostate cancer cell growth in both the presence of hormone and under androgen-deprived conditions.

Example 7

DDC Inhibitors Decrease the Rate of Cell Growth of Androgen-Independent C4-2 Cells In Vitro Description of Study Procedures
Cell Proliferation Assay Cell proliferation assays were performed using the 3-(4,5-dimethylthiazol-2-yl)-5-(3-carboxymethoxyphenyl)-2-(4-sulfophenyl)-2H-tetrazolium Assay (MTS) according to the manufacturer's protocol, with minor modifications (Promega). C4-2 cells were plated in 96-well plates at a density of 750 cells per well in RPMI medium containing 5% CSS for 1 day. On the following day, the DDC inhibitors, carbidopa (25 μM) and NSD-1015 (10 μM)±0.1 nM R1881 were added to each well in charcoal-stripped serum (CSS; Hyclone, VWR) RPMI media. The cells were harvested at days 0, 2, 4, and 6, with a medium change every 3 days. Each time point was measured with 6 replicates.

Statistical Analysis

Student's t-test (two-sample equal variance) was used to evaluate statistically significant differences. All calculated p-values were two-sided and those less than 0.05 were considered statistically significant.

Results and Interpretation

Figure 11A:
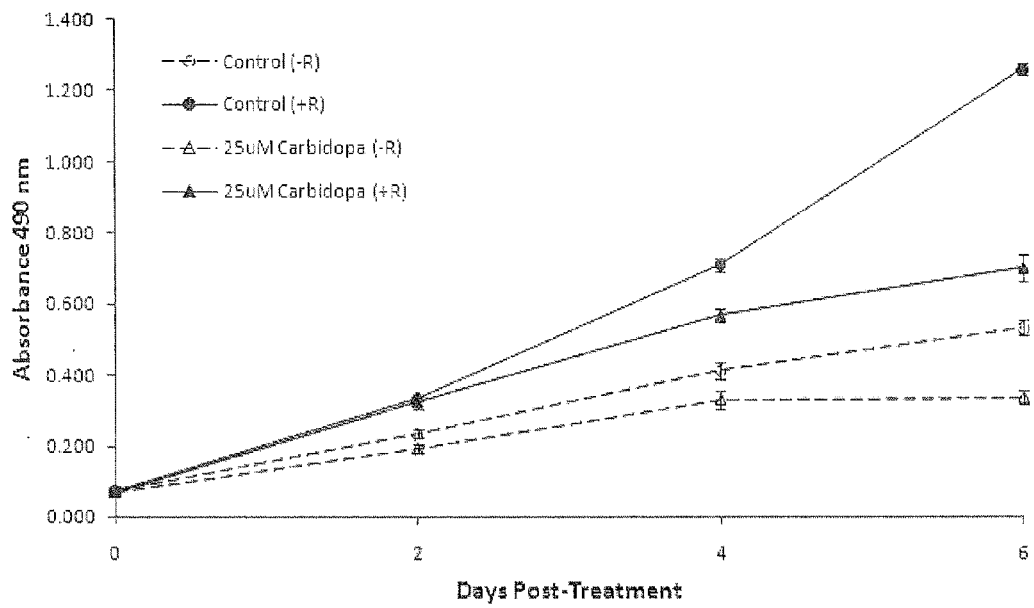
FIG. 11 shows the effects of DDC inhibitors on the growth of androgen-independent C4-2 cells.
Figure 11B:
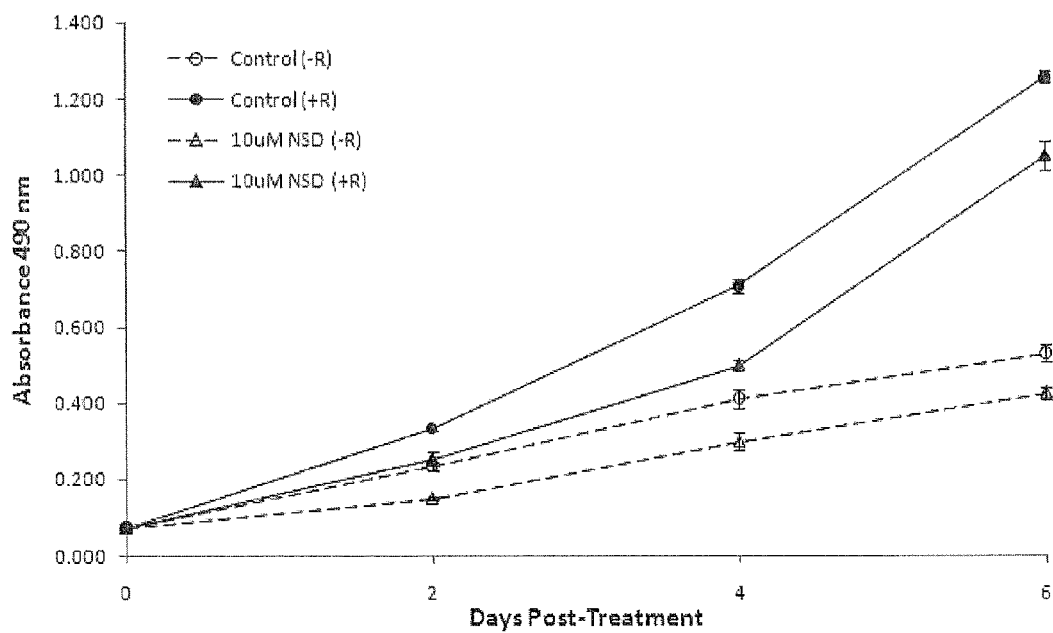

To assess the effects of DDC enzymatic inhibitors on the growth of androgen-independent prostate cancer cells, the C4-2 cell line, which is derived from chimeric LNCaP/MS (human osteosarcoma line) tumours passaged twice in castrated male mice (Wu et al., Int J Cancer 1994; 57: 406-412), was utilized. These C4-2 cells represent an androgen-independent form of LNCaP cells, which express endogenous DDC, but have the capacity to grow in androgen-deprived conditions and express AR, as well as secrete PSA. Thus, C4-2 cells can be used as an ideal model to study the role of the DDC-AR interaction in a castration-resistant setting that resembles clinical disease. Treatment of C4-2 cells with 25 μM carbidopa resulted in a significant inhibition of growth such that by day 6 of treatment the number of cells were reduced by 1.58-fold in the absence of androgen and by 1.80-fold in the presence of androgen relative to the control non-treated cells (FIG. 11A). Similarly, exposing C4-2 cells to another DDC inhibitor (6 days), NSD-1015 (10 μM concentration), also caused a significant reduction in cell growth, with a 1.20-fold decrease in the absence of hormone and a 1.24-fold decline in the presence of hormone (FIG. 11B). Overall, these data indicate that inhibition of DDC enzymatic activity, via more than one inhibitor, can substantially reduce the growth of androgen-independent prostate cancer cells in the presence of androgens but also under the androgen-deprived conditions that mimic hormone refractory prostate tumours.

Example 8

DDC Increases AR Transactivation and Tumour Growth In Vivo and Inhibition of DDC Enzymatic Activity with Carbidopa Reverses this Effect Description of Study Procedures
Plasmid Construction To generate a DDC-lentiviral expression construct, pENTR-DDC plasmid (containing coding region of DDC cloned into pDONR201, as described previously) was used for a recombination reaction with pLenti4/TO/V5-DEST vector (Gateway™ Technology, Invitrogen) to generate the pLenti4/TO/V5-DEST-DDC plasmid. Due to the presence of a stop codon in pENTR-DDC, the C-terminus of DDC was not V5-tagged in the DDC-lentiviral construct.

Generation of Tetracycline-Inducible DDC LNCaP Cells

Stable cell lines that expressed DDC under tetracycline control were generated using the ViraPower™ T-Rex™ Lentiviral Expression System, Version A (Invitrogen), according to the manufacturer's protocol. Briefly, the pLenti4/TO/V5-DEST-DDC plasmid, pLenti4/TO/V5-DEST empty control vector (contain zeocin selection) and the pLenti6/TR Tet repressor plasmid (contains Blasticidin selection) were co-transfected individually with the lentiviral ViraPower™ Packaging Mix plasmids (pLP1, pLP2, pLP/VSVG) into 293FT cells using Lipofectamine 2000 reagent (Invitrogen). After 48 hours, conditioned medium containing virus was filtered and stored at −80° C. A control lentiviral pHR-CMV-EGFP plasmid was also used with the pLP1, pLP2 and pLP/VSVG packaging plasmids for production of EGFP (enhanced green fluorescent protein) retroviral particles. Viral concentration for all utilized lentiviral vectors was determined using an ELISA assay for the p24 viral protein, as previously reported. LNCaP cells were co-transduced with TR virus and either DDC or Lenti4/TO/V5-DEST control vector viral particles. Lentiviral infection was also carried out with the EGFP virus and EGFP-positive cells were counted using a fluorescent microscope (Carl Zeiss) for determination of infection efficiency.

The multiplicity of infection (MOI) used for LNCaP cells was 50-60. Infected cells were selected by varying concentrations of Zeocin and Blasticidin (Invitrogen). Induction of DDC protein expression in LNCaP cells was initially verified by Western blot analysis after treating cells for 48 hours with 1 μg/mL of the tetracycline analogue, doxycycline hyclate (Dox; Sigma).

LNCaP-DDC Tumour Xenografts and Carbidopa Treatment

LNCaP-DDC and LNCaP-Vector control cells were inoculated subcutaneously (s.c.), after resuspension in 0.1 mL of Matrigel (Becton Dickinson Labware), into two flank regions ($2.5 \times 10^6$ cells/site) of 6 to 8 week old male athymic nude mice (Harlan Sprague Dawley, Inc.) via a 27-gauge needle under halothane anesthesia. Tumour volume and serum PSA measurements (blood collected from the tail vein) were performed once per week after tumours became palpable. PSA levels were measured by ELISA (ClinPro International) and tumour size was calculated by the formula; length×width×depth×0.5236. Once serum PSA values reached 75-100 ng/mL, mice in both the LNCaP-DDC and LNCaP-Vector control groups were given Dox-treated water (200 μg/mL) and treated with or without carbidopa. Carbidopa was purchased from Sigma and dissolved in DMSO. The solution was diluted in PBS to a final concentration of 10% DMSO and sterilized through a 0.2 μm filter. Carbidopa solution was injected intraperitoneally into half of the mice (25 mg per kg of body weight) for the +carbidopa groups, while the remaining mice received vehicle injections consisting of 10% DMSO in PBS (−carbidopa groups). Injections were carried out daily for the duration of the experiment. Each animal group contained a minimum of 4 mice, with a range of 4-6 mice. PSA measurements were used to calculate PSA velocity and volume measurements were used to determine the tumour growth rate for all groups with linear regression slope analysis (see Statistical Analysis below). PSA velocity was defined as the increase in PSA level (normalized to pre-treatment value set at 100%) divided by number of days that PSA was reliably measurable (35 days). Tumour growth rate was defined as the increase in tumour volume (normalized to pre-treatment value set at 100%) divided by the duration (49 days) of the experiment. All animal procedures were performed according to the guidelines of the Canadian Council of Animal Care and with appropriate institutional certification.

Western Blot Analysis

All SDS-PAGE and Western blot analyses were performed as previously described. Briefly, detection of His-DDC protein in GST-pulldown assays was carried out using the rabbit polyclonal anti-DDC antibody (Chemicon). Detection of AR, DDC and β-actin for PC3/LNCaP cell transactivation assays was performed with the mouse monoclonal anti-AR441 (Santa Cruz), rabbit polyclonal anti-DDC (Chemicon) and rabbit polyclonal anti-β-actin (Sigma) antibodies, respectively. The final concentration of all primary antibodies was 1 μg/mL. These antibodies were also used for detection of DDC and β-actin in LNCaP-DDC and LNCaP-Vector control tumour xenografts (−/+carbidopa). Tumour protein extracts were prepared by removing tumour tissue from hosts at the end of experiments, flash frozen in liquid nitrogen and Dounce homogenized on ice using RIPA lysis buffer. Protein extracts were quantified by BCA assay (Pierce Biotechnology, Inc.) and used for SDS-PAGE/Western blot analysis.

Statistical Analysis

LNCaP-DDC and LNCaP-Vector control xenograft tumour volume and PSA values (−/+carbidopa) were used for linear regression slope analysis to determine PSA velocity and tumour growth rate with GraphPad Prism 4, version 4.03. PSA velocity and tumour growth rate differences were determined by one-way ANOVA and Tukey's multiple comparison test. All other statistical analysis was performed using the Student's t-test (two-sample equal variance) with JMPIN statistical software (Version 4.0.2, SAS Institute Inc.). All calculated p-values were two-sided and those less than 0.05 were considered statistically significant.

Results and Interpretation

LNCaP-DDC and LNCaP-Vector control stable cells were injected into mice and long-term PSA production/tumour growth were measured in the presence of Dox with or without carbidopa treatment. In these LNCaP tumour xenografts, the effect of DDC on in vivo AR transcriptional activity was analyzed first (FIG. 4A). AR drives the transcription of PSA, and there was a significant increase in PSA velocity (rate of PSA production) between the vector control (18.5±1) and DDC overexpression (29.4±4) groups over 35 days. Treating mice bearing DDC overexpressing LNCaP tumours with carbidopa, reduced PSA velocity significantly back to a level (14.7±0.6) that was not statistically different from the vector control group. This observation suggests that carbidopa can indeed reverse the in vivo coactivation effect of DDC seen when the enzyme is overexpressed. Notably, when the vector control group expressing only endogenous levels of DDC protein was treated with carbidopa, there was also a significant decrease (from 18.5±1 to 7.2±1) in PSA velocity, demonstrating that low level endogenous DDC expression and activity is important for AR transactivation in LNCaP tumours. These data suggest that DDC can enhance in vivo AR transcriptional activity, as measured by the endogenous PSA marker, with sustained long-term overexpression of the coactivator, an effect that can be reversed by the enzymatic DDC inhibitor, carbidopa.

DDC also affected the rate of tumour growth in LNCaP xenografts (FIG. 4B). DDC overexpression significantly increased tumour growth rate from 27.9±2 for the vector control group to 50.1±3 for the DDC group over 49 days. Treatment of LNCaP-DDC mice with carbidopa reduced tumour growth to within the same range (22.5±3) as the vector control group. As seen for PSA velocity above, treating the vector control mice with carbidopa also significantly reduced tumour growth rate (from 27.9±2 to 9.8±2) over the course of the experiment. These data demonstrate that DDC can facilitate LNCaP tumour growth and that inhibiting its enzymatic activity with carbidopa can substantially reduce the growth promoting effects of DDC.

Western blot analysis of LNCaP tumours in xenografts revealed that LNCaP-DDC cells maintained stable DDC overexpression in the presence of Dox (with and without carbidopa treatment) and the ~50 kDa protein was present after long-term in vivo growth (FIG. 5). Western blot analysis using tumours that did not overexpress DDC (LNCaP-Vector Control group) showed that LNCaP cells express low endogenous levels of DDC protein.

Example 9

Carbidopa Treatment of LNCaP Tumours in Castrated Mice Delays Progression to Androgen-Independence and Retards Tumour Growth Description of Study Procedures LNCaP Tumour Xenografts and Carbidopa Treatment Parental LNCaP cells were inoculated subcutaneously (s.c.), after resuspension in 0.1 mL of Matrigel (Becton Dickinson Labware), into two flank regions ($2.5 \times 10^6$ cells/site) of 6 to 8 week old male athymic nude mice (Harlan Sprague Dawley, Inc.) via a 27-gauge needle under halothane anesthesia. Tumour volume and serum PSA measurements (blood collected from the tail vein) were performed once per week after tumours became palpable. PSA levels were measured by ELISA (ClinPro International) and tumour size was calculated by the formula; length×width×depth×0.5236.

Once serum PSA values reached 75-100 ng/mL, mice were castrated and treated with or without carbidopa. Carbidopa was purchased from Sigma and dissolved in DMSO. The solution was diluted in PBS to a final concentration of 10% DMSO and sterilized through a 0.2 μm filter. Carbidopa solution was injected intraperitoneally into half of the mice (25 mg per kg of body weight) for the +carbidopa group, while the remaining mice received vehicle injections consisting of 10% DMSO in PBS (−carbidopa group). Injections were carried out daily for the duration of the experiment. Each animal group contained 5-6 mice. Serum PSA and tumour volume values were measured with progression to androgen-independence and normalized to pretreatment values (set at 100%) to obtain the mean percentage PSA and mean tumour volume of pre-treatment (±SEM). All animal procedures were performed according to the guidelines of the Canadian Council of Animal Care and with appropriate institutional certification.

Statistical Analysis

Statistical analysis was performed using the Student's t-test (two-sample equal variance) with JMPIN statistical software (Version 4.0.2, SAS Institute Inc.). All calculated p-values were two-sided and those less than 0.05 were considered statistically significant.

Results and Interpretation

Figure 12A:
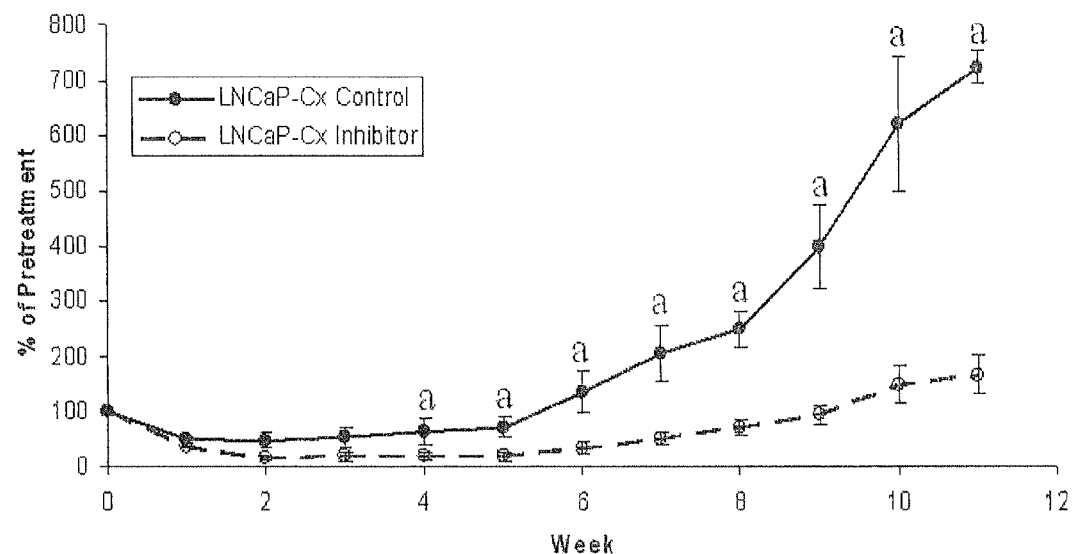
FIGS. 12A-B show the effect of carbidopa DDC inhibitor on serum PSA and tumour growth of parental LNCaP xenografts in castrated mice.

In the LNCaP tumour xenograft model, the effect of carbidopa was tested on the rate of progression to androgen-independence (AI), defined as the time required after castration for PSA levels to return to or increase above pre-castrate levels (FIG. 12A). As expected, castration of the parental LNCaP control group (−carbidopa Control) resulted in a decrease of serum PSA within one week (50±6% of pre-treatment), before rising to pre-treatment levels between weeks 5 and 6 (136±39% at week 6). Treatment of castrated mice with carbidopa (Inhibitor group) reduced PSA levels to 38±5% of pre-treatment at week 1, reaching AI between weeks 9 and 10 (148±34% at week 10). The significant decrease in PSA levels with carbidopa treatment was maintained under castration conditions until termination of the experiment (11 weeks), at which point the control group exhibited a PSA level of 723±29% of pre-treatment, while that of the inhibitor group was only 167±36% (4.3-fold decrease with carbidopa treatment). These data suggest that inhibiting endogenous DDC enzymatic activity with carbidopa can significantly repress in vivo AR transcriptional activity (measured by the PSA marker) and delay progression to AI in the LNCaP tumour model.

Figure 12B:
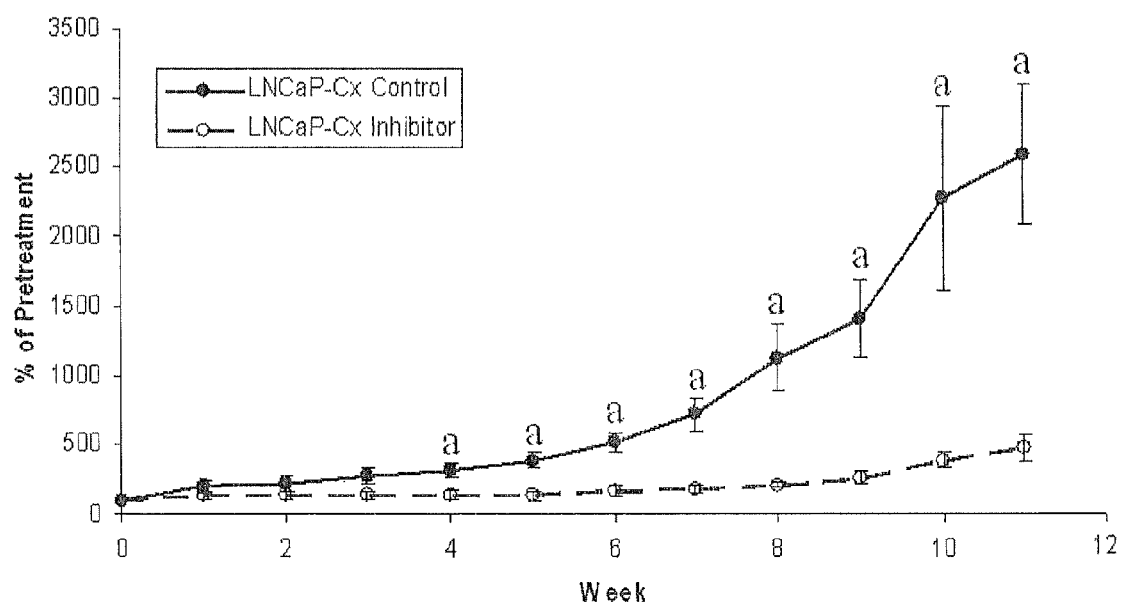

DDC also affected tumour growth in parental LNCaP xenografts (FIG. 12B). Comparison of tumour volumes for the LNCaP control and inhibitor groups at 11 weeks revealed that carbidopa treatment of castrated mice significantly decreased tumour growth by 5.4-fold from 2589±503% of pre-treatment for the control group to 478±97% for the inhibitor group. For the control group, tumour volume increased from pre-treatment volume by approximately 26-fold over 11 weeks, whereas for the carbidopa inhibitor group this increase was only about 5-fold. Overall, the substantial decrease in tumour growth with carbidopa treatment indicates that the inhibition of catalytic activity of endogenous DDC protein is sufficient to retard tumour growth.

Example 10

Carbidopa Treatment of Androgen-Independent C4-2 Tumours in Pre-Castrated Mice Reduces PSA Production and Retards Tumour Growth Description of Study Procedures C4-2 Tumour Xenografts and Carbidopa Treatment Parental C4-2 cells were inoculated subcutaneously (s.c.), after resuspension in 0.1 mL of Matrigel (Becton Dickinson Labware), into two flank regions ($2.5\times10^6$ cells/site) of 6 to 8 week old castrated (to ensure tumors will be androgen-independent) male athymic nude mice (Harlan Sprague Dawley, Inc.) via a 27-gauge needle under halothane anesthesia. Tumour volume and serum PSA measurements (blood collected from the tail vein) were performed once per week after tumours became palpable. PSA levels were measured by ELISA (ClinPro International) and tumour size was calculated by the formula; length×width×depth×0.5236.

Once serum PSA values reached 75-100 ng/mL, mice were treated with or without carbidopa. Carbidopa was purchased from Sigma and dissolved in DMSO. The solution was diluted in PBS to a final concentration of 10% DMSO and sterilized through a 0.2 μm filter. Carbidopa solution was injected intraperitoneally into half of the mice (25 mg per kg of body weight) for the +carbidopa groups, while the remaining mice received vehicle injections consisting of 10% DMSO in PBS (−carbidopa groups). Injections were carried out daily for the duration of the experiment. Each animal group contained 2-3 mice. PSA measurements were used to calculate PSA velocity and volume measurements were used to determine the tumour growth rate for all groups with linear regression slope analysis (see Statistical Analysis below). PSA velocity was defined as the increase in PSA level (normalized to pre-treatment value set at 100%) divided by number of days that PSA was reliably measurable (21 days). Tumour growth rate was defined as the increase in tumour volume (normalized to pre-treatment value set at 100%) divided by the duration (21 days) of the experiment. All animal procedures were performed according to the guidelines of the Canadian Council of Animal Care and with appropriate institutional certification.

Statistical Analysis

C4-2 xenograft tumour volume and PSA values (−/+carbidopa) were used for linear regression slope analysis to determine PSA velocity and tumour growth rate with GraphPad Prism 4, version 4.03. PSA velocity and tumour growth rate differences were determined using the Student's t-test. All calculated p-values were two-sided and those less than 0.05 were considered statistically significant.

Results and Interpretation

Figure 13A:
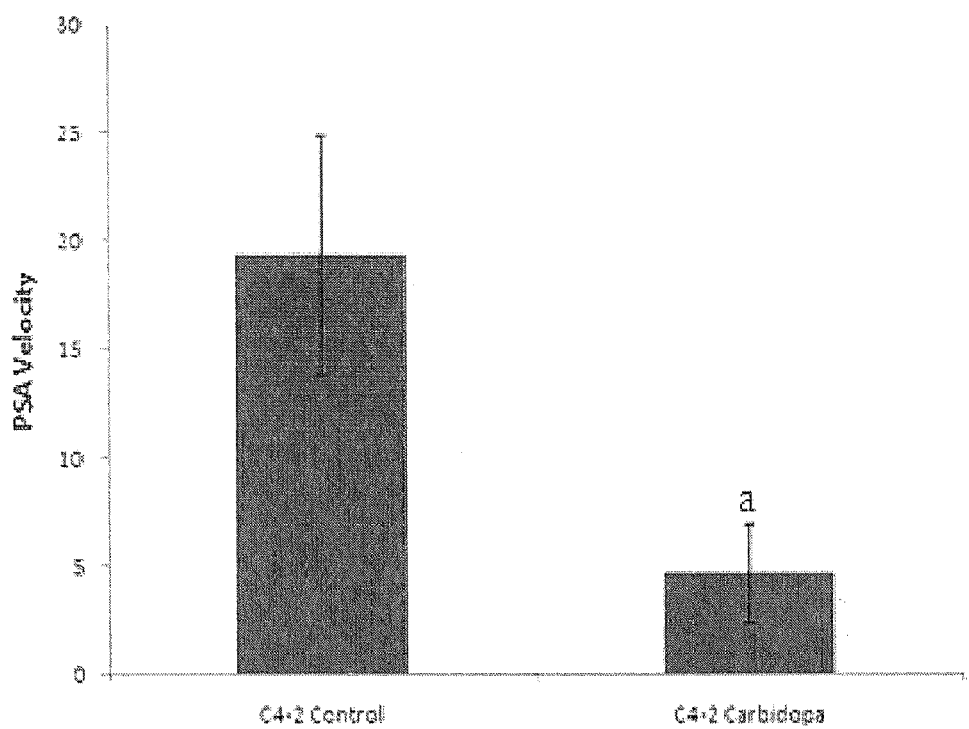
FIGS. 13A-B depict the effect of carbidopa treatment on serum PSA and tumour growth in androgen-independent C4-2 xenografts.
Figure 13B:
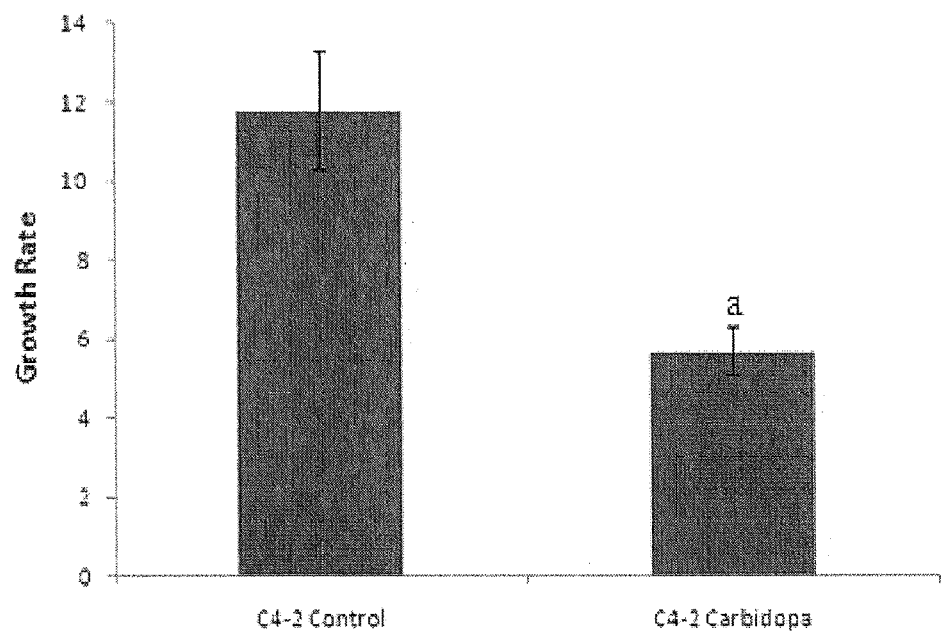

To assess whether carbidopa can be used as an effective therapy to treat prostate tumours that have progressed to androgen independence, the C4-2 xenograft model was utilized. Compared to the LNCaP androgen-dependent xenograft model, in which LNCaP cells must be injected into non-castrated mice in order to develop tumours, in the androgen-independent prostate cancer model, C4-2 cells that can grow in the absence of androgens are injected into pre-castrated mice. These tumours represent castration-resistant clinical prostate cancers and express AR, as well as produce PSA, even under androgen-deprived castration conditions. Hence, the C4-2 xenograft model is a useful system for determining the effects of DDC on AR function, PSA production and tumour growth in an androgen-independent setting that mimics hormone refractory prostate cancers. Parental C4-2 cells were injected into pre-castrated mice, which were treated with or without carbidopa and PSA production/tumour growth were measured. There was a significant decrease (4.1 fold) in PSA velocity (rate of PSA production) between the control non-treated (19.4±5) and carbidopa treated (4.7±2) mice over 21 days (FIG. 13A). Treating mice bearing C4-2 tumours with carbidopa also reduced tumour growth rate by 2.1 fold from 11.8±1 to 5.7±0.6 (FIG. 13B). The above results demonstrate that inhibiting the enzymatic activity of endogenous DDC protein in C4-2 xenografts can reduce PSA production and the growth rate of these castration-resistant prostate tumours.

FIGURE LEGENDS

FIG. 1A—depicts that DDC enhances AR transcription from the PSA promoter. PC3 cells were transfected with human AR expression plasmid (250 ng/well), pRL-TK-renilla (83 ng/well) and pPSA-630 bp-Luc or pARR3-tk-Luc synthetic reporter for comparison (167 ng/well). The amount of transfected pDEST12.2-DDC plasmid (1 µg/well) was four times that of AR (AR:DDC ratio of 1:4). Total DNA was kept constant at 1.5 µg/well using pDEST12.2 empty vector control (1:0 ratio). Cells were treated with or without 1 nM R1881 for 24 hours before harvest and luciferase assay. Transfection efficiency was normalized with the renilla luciferase pRL-TK vector. RLU values are the mean of triplicates (±SEM); $^a p<0.05$ as compared to −R1881 control for pPSA-630 bp-Luc reporter, $^b p<0.05$ as compared to −R1881 control for pARR3-tk-Luc reporter, $^c p<0.05$ as compared to +R1881 empty vector control (1:0 ratio) for pPSA-630 bp-Luc and $^d p<0.05$ as compared to +R1881 empty vector control (1:0 ratio) for pARR3-tk-Luc. Each graph is representative of 3 independent trials.

Figure 1B:
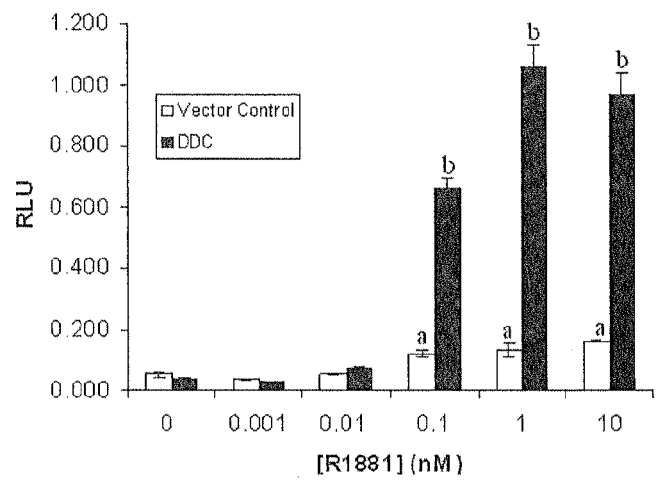

FIG. 1B-depicts that DDC sensitizes AR to limiting androgen concentrations in PC3 cells. PC3 cells were transfected as above using the pARR3-tk-Luc reporter. After transfection, cells were incubated for 24 hours in absence or presence of increasing concentrations of R1881. Firefly luciferase values were normalized to renilla luciferase and the mean RLU values of triplicates (±SEM) are shown; $^a p<0.05$ as compared to −R1881, 0.001 nM and 0.01 nM R1881 and $^b p<0.05$ as compared to 0.1 nM, 1 nM and 10 nM R1881 of empty vector control.

Figure 1C:
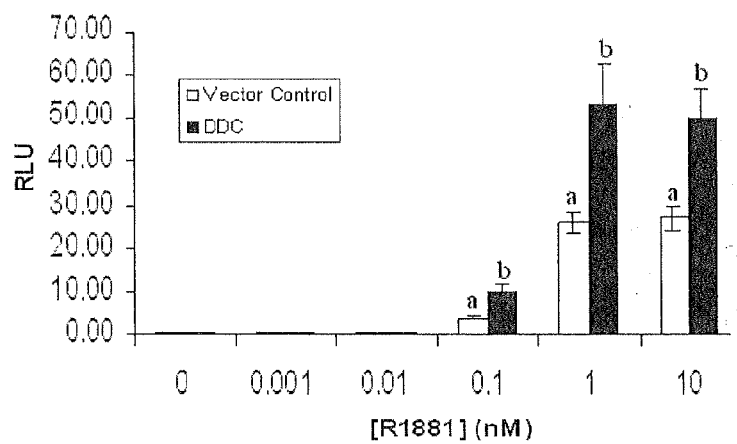

FIG. 1C—depicts that DDC sensitizes AR to limiting androgen concentrations in LNCaP cells. LNCaP cells were transfected as above using the pARR3-tk-Luc reporter, except AR was not included. After transfection, cells were incubated for 24 hours in absence or presence of increasing concentrations of R1881. Firefly luciferase values were normalized to renilla luciferase and the mean RLU values of triplicates (±SEM) are shown; $^a p<0.05$ as compared to −R1881, 0.001 nM and 0.01 nM R1881 and $^b p<0.05$ as compared to 0.1 nM, 1 nM and 10 nM R1881 of empty vector control.

FIG. 2A—depicts that purified His-DDC protein interacts with the AR-LBD. GST protein and GST-AR domain fusion proteins (DBD+LBD and DBD alone) were coupled to glutathione-agarose beads at equimolar levels (see FIG. 9 for Coomassie Blue stain of GST-AR domains). Purified His-DDC protein was incubated (0.5 µg/assay) with GST-AR domains and bound protein was detected via SDS-PAGE/Western blot analysis using an anti-DDC antibody.

FIG. 2B-depicts that purified His-DDC protein enhances apparent affinity of AR for androgen in vitro. Ligand binding assays were performed using AR-LBD protein (1 µg/assay) and increasing R1881 concentrations, with 20 nM [$^3$H]-R1881 as tracer. Assays were carried out in the absence (R1881 control) and presence of His-DDC protein (0.5 µg/assay). Results are shown for the 10 nM, 100 nM and 1000 nM concentrations of R1881, expressed as the mean total pmole bound R1881/mg AR-LBD protein from three replicates (±SEM); $^a p<0.05$ as compared to corresponding 100 nM and 1000 nM R1881 concentrations of the R1881 control. The concentrations of R1881 required, in the absence and presence of His-DDC, to 50% saturate total AR-LBD protein (equivalent of 10,000 pmole bound R1881/mg AR-LBD protein) was determined using linear regression analysis (GraphPad InStat, Version 3.06).

FIG. 3A-depicts that DDC increases maximum androgen-binding capacity of AR in the cytosol of HeLa-AR cells. Cytosolic cell extracts were prepared from HeLa-AR cells that were transfected with pDEST12.2-DDC or pDEST12.2 control vector and treated with increasing concentrations of [$^3$H]-R1881 for 24 hours. FLAG-tagged AR was immunoprecipitated from protein lysates using agarose beads conjugated to a FLAG monoclonal antibody and the amount of specifically bound [$^3$H]-R1881 to AR was measured (dpm) using a scintillation counter. Aliquots (10%) of cytosolic lysates were also subjected to Western blotting (anti-AR antibody) to determine FLAG-tagged AR protein levels, which was used for normalization of measured dpm values (described in the Examples section). Results are expressed as the relative mean bound ligand (dpm) of three replicates (±SEM); $^a p<0.05$ as compared to corresponding 1 nM and 10 nM [$^3$H]-R1881 concentrations of vector control. The concentrations of [$^3$H]-R1881 required, with and without DDC overexpression, to reach the vector control $B_{max}$ (maximum androgen-binding capacity) was determined using linear regression analysis (GraphPad InStat, Version 3.06).

FIG. 3B—depicts that cytosolic DDC increases the level of nuclear androgen-bound AR in HeLa-AR cells. Nuclear fraction cell extracts were prepared from HeLa-AR cells that were transfected with pDEST12.2-DDC or pDEST12.2 control vector and treated with increasing concentrations of [$^3$H]-R1881 for 24 hours. FLAG-tagged AR was immunoprecipitated from protein lysates using agarose beads conjugated to a FLAG monoclonal antibody and the amount of specifically bound [$^3$H]-R1881 to AR was measured (dpm) using a scintillation counter. Aliquots (10%) of nuclear lysates were also subjected to Western blotting (anti-AR antibody) to determine FLAG-tagged AR protein levels, which was used for normalization of measured dpm values (described in the Examples section). Results are expressed as the relative mean bound ligand (dpm) of three replicates (±SEM); $^a p<0.05$ as compared to corresponding 1 nM and 10 nM [$^3$H]-R1881 concentrations of vector control. The concentrations of [$^3$H]-R1881 required, with and without DDC overexpression, to reach the vector control $B_{max}$ was determined using linear regression analysis (GraphPad InStat, Version 3.06).

FIG. 3C—depicts that DDC does not increase cellular androgen-uptake in HeLa-AR Cells. Androgen cellular-uptake assays were performed using HeLa-AR cells that were transfected with either pDEST12.2-DDC or pDEST12.2 control vector and incubated for 24 hours with increasing concentrations of [$^3$H]-R1881. Whole cell extracts were prepared with RIPA buffer and used for scintillation counting to determine cellular [$^3$H]-R1881 accumulation (dpm/well of 6-well plate). Results are expressed as the mean specific cellular [$^3$H]-R1881 uptake of three replicates (±SEM).

FIG. 4A—depicts that carbidopa treatment reduces serum PSA levels in LNCaP-DDC and LNCaP-Vector control xenografts. LNCaP-DDC and LNCaP-Vector control cells were inoculated subcutaneously into male nude mice with weekly monitoring of serum PSA. Once serum PSA values reached 75-100 ng/mL, the animals received Dox-treated water and were injected intraperitoneally with carbidopa (25 mg/kg) or vehicle consisting of 10% DMSO in PBS. Measured serum PSA values were normalized to pretreatment values (set at 100%) to obtain the mean percentage PSA of pre-treatment (±SEM). The increase in PSA level was divided by the number of elapsed days (35 days) to determine PSA velocity for each group (linear regression slope analysis, GraphPad Prism 4); $^a$p<0.05 as compared to the vector control group (+carbidopa), $^b$p<0.05 as compared to vector control (−carbidopa) and $^c$p<0.05 as compared to DDC (+carbidopa).

FIG. 4B—depicts that treatment of LNCaP-DDC and LNCaP-Vector control mice with carbidopa reduced xenograft tumour growth LNCaP-DDC and LNCaP-Vector control cells were inoculated subcutaneously into male nude mice with weekly monitoring of serum PSA and tumour volumes. Once serum PSA values reached 75-100 ng/mL, the animals received Dox-treated water and were injected intraperitoneally with carbidopa (25 mg/kg) or vehicle consisting of 10% DMSO in PBS. Measured tumour volume values were normalized to pretreatment values (set at 100%) to obtain the mean percentage tumour volume of pre-treatment (±SEM). The increase in tumour volume was divided by the number of elapsed days (49 days) to determine growth rates for each group (linear regression slope analysis, GraphPad Prism 4); $^a$p<0.05 as compared to the vector control group (+carbidopa), $^b$p<0.05 as compared to vector control (−carbidopa) and $^c$p<0.05 as compared to DDC (+carbidopa).

FIG. 5—depicts that endogenous and induced DDC levels exist in LNCaP-Vector control and LNCaP-DDC xenografts in the presence and absence of carbidopa. Whole cell protein extracts were prepared in RIPA buffer from tumours at various time points and used for Western blot analysis (50 μg protein/well) with an anti-DDC antibody (β-actin blotting was used for loading control). Results are shown for LNCaP-DDC and LNCaP-Vector control tumours treated with or without carbidopa in the presence of Dox. For the LNCaP-DDC group, lanes 1 and 2 show representative levels of DDC overexpression for two mice treated with carbidopa, while lanes 3 and 4 represent DDC protein levels in two non-treated mice. For the LNCaP-Vector Control group, lanes 1 and 2 show endogenous DDC expression for two mice with carbidopa treatment, while lanes 3 and 4 show DDC expression in the absence of carbidopa (lane 5 is a positive control for detecting endogenous DDC protein; 2 ug of protein extract from a LNCaP-DDC mouse not treated with carbidopa).

FIG. 6A—depicts the effect of DA on Induction of Intracellular cAMP Levels in PC3 and LNCaP Cells. DA was used to treat PC3 and LNCaP cells in serum-free DMEM and RPMI media. Cells were stimulated with DA for 15 minutes and cell lysates from triplicate wells (12-well plate) were used for cAMP analysis by ELISA. Results are expressed as the mean cAMP concentration (fmol/well) ±SEM; $^a$p<0.05 as compared to control PC3 cells not treated with DA. Levels of cAMP were also normalized to mass (μg) of whole cell lysate protein (fmol/μg protein), which followed the same trend as above.

FIG. 6B—depicts the effect of 5-HT on Induction of Intracellular cAMP Levels in PC3 and LNCaP Cells. 5-HT was used to treat PC3 and LNCaP cells in serum-free DMEM and RPMI media. Cells were stimulated with 5-HT for 10 minutes and cell lysates from triplicate wells (12-well plate) were used for cAMP analysis by ELISA. Results are expressed as the mean cAMP concentration (fmol/well) ±SEM. Levels of cAMP were also normalized to mass (μg) of whole cell lysate protein (fmol/μg protein), which followed the same trend as above.

FIG. 7A—depicts that DDC coactivation of AR transcription is independent of DA neurotransmitter using an ELISA for DA. Dopamine ELISA; PC3 cells were transfected with AR expression plasmid (125 ng/well) and pDEST12.2-DDC (0.5 μg/well) or pDEST12.2 empty vector control (0.5 μg/well) to mimic previous transactivation assays (AR:DDC ratio of 1:4 versus 1:0). Cells were treated with 1 nM R1881 for 24 hours in the presence and absence of 1 μM NSD-1015 DDC enzymatic inhibitor. PC12 cells were not transfected or treated with R1881 but were incubated 24 hours with or without NSD-1015. Conditioned media (CM) was collected from PC3 and PC12 cells for DA ELISAs. Secreted DA levels (pg) were normalized to the assayed volume of CM (0.1 mL) and are expressed as the mean of triplicates (±SEM); $^a$p<0.05 as compared to 0 NSD-1015 for PC12 cells.

FIG. 7B—depicts that DDC coactivation of AR transcription is independent of DA neurotransmitter using a transactivation assay. Dopamine transactivation assay; PC3 cells were transfected with AR expression plasmid, pRL-TK-renilla and pARR3-tk-Luc reporter. Cells were treated with or without 1 nM R1881 and increasing concentrations of pure DA for 24 hours before harvest and luciferase assay. RLU values were obtained by normalizing to total protein concentration and are presented as the mean of triplicates (±SEM); $^a$p<0.05 as compared to +R1881/−DA control. This graph is representative of 3 independent trials.

FIG. 8A—depicts that mtDDC does not coactivate AR transactivation in PC3 cells in the presence of androgen. PC3 cells were transfected with a constant amount of AR (250 ng/well), pARR3-tk-Luc (167 ng/well), pRL-TK-renilla (83 ng/well) and increasing amounts of pDEST12.2-DDC (wt) or pDEST12.2-mt-DDC (mt) vector. These amounts included 0, 0.5 or 1.0 μg/well, which correspond to the 1:0, 1:2 and 1:4 AR:DDC ratios, respectively. Total DNA was kept constant at 1.5 μg/well using pDEST12.2 empty vector control. Cells were treated with or without 1 nM R1881 for 24 hours prior to harvest and luciferase assay (results above only show +R1881 conditions for clarity; in the absence of R1881 AR activity was virtually undetectable). The renilla luciferase pRL-TK vector was used for normalization of transfection efficiency. RLU values are the mean of triplicates (±SEM); $^a$p<0.05 as compared to +R1881 empty vector control (1:0 ratio) and $^b$p<0.05 as compared to +R1881 1:2 AR:DDC ratio. The graph is representative of 3 independent trials.

FIG. 8B—depicts that mtDDC does not coactivate AR transactivation in LNCaP cells in the presence of androgen. LNCaP cells were transfected with a constant amount of pARR3-tk-Luc (167 ng/well), pRL-TK-renilla (83 ng/well) and increasing amounts of pDEST12.2-DDC (wt) or pDEST12.2-mt-DDC (mt) vector. These amounts included 0, 0.5 or 1.0 μg/well, which correspond to the 0:0, 0:2 and 0:4 AR:DDC ratios, respectively. Total DNA was kept constant at 1.5 μg/well using pDEST12.2 empty vector control. Cells were treated with or without 1 nM R1881 for 24 hours prior to harvest and luciferase assay (results above only show +R1881 conditions for clarity; in the absence of R1881 AR activity was virtually undetectable). The renilla luciferase pRL-TK vector was used for normalization of transfection efficiency. Mean RLU values (±SEM) are presented; $^a$p<0.05 as compared to +R1881 empty vector control (0:0 ratio). The graph is representative of 3 independent trials.

FIG. 8C—depicts that the expression level of mtDDC and wtDDC proteins were similar during the transactivation assay in PC3 cells. PC3 cell transactivation assay protein lysates were used to determine AR and wt DDC versus mt DDC expression levels. A 10 μg aliquot of protein lysate from each triplicate assay was combined (30 μg total protein) and subjected to SDS-PAGE/Western blot analysis. Blots were probed with anti-AR, anti-DDC and anti-β-actin antibodies.

FIG. 8D—depicts that the expression level of mtDDC and wtDDC proteins were similar during the transactivation assay in LNCaP cells. LNCaP cell transactivation assay protein lysates were used to determine AR and wt DDC versus mt DDC expression levels. A 10 μg aliquot of protein lysate from each triplicate assay was combined (30 μg total protein) and subjected to SDS-PAGE/Western blot analysis. Blots were probed with anti-AR, anti-DDC and anti-β-actin antibodies.

FIG. 9—depicts that the interaction of DDC with AR is independent of its enzymatic activity. GST protein and GST-AR domain fusion proteins (Truncated-NTD+LBD, DBD and DBD+LBD) were coupled to glutathione-agarose beads at equimolar levels, as determined by Coomassie Blue staining (GST-AR domains). Wt DDC and mt DDC were expressed by in vitro transcription/translation and radio labeled using [$^{35}$S]-methionine. After incubation of radiolabeled proteins and GST-AR domains, bound protein was eluted for SDS-PAGE and autoradiography analysis.

FIGS. 10A and 10B. Effects of DDC inhibitors on the growth of androgen-dependent LNCaP cells. MTS assays were performed on LNCaP cells grown in the presence of DDC inhibitors carbidopa and NSD. LNCaP cells were plated in 96-well plates (3000 cell/well) and incubated in RPMI medium containing 5% CSS for one day. Cells were either treated with 25 and 50 μM carbidopa (FIG. 10A) or with 10 μM NSD-1015 (FIG. 10B), in the absence or presence of 0.1 nM R1881. Cell numbers were assayed at various times using MTS assay. Absorbance at 490 nm versus time for each treatment was plotted. The results are presented as mean±S.E. of 6 replicates.

FIGS. 11A and 11B. Effects of DDC inhibitors on the growth of androgen-independent C4-2 cells. MTS assays were performed on C4-2 cells grown in the presence of DDC inhibitors carbidopa and NSD. C4-2 cells were plated in 96-well plates (750 cell/well) in RPMI medium containing 5% CSS for 1 day. 25 μM carbidopa (FIG. 11A) or 10 μM NSD (FIG. 11B) ±0.1 nM R1881 was added to the cells. MTS assays were performed at various intervals and absorbance at 490 nm versus time was plotted. The results are presented as mean±S.E. of 6 replicates.

FIG. 12A—Effect carbidopa DDC inhibitor on serum PSA of parental LNCaP xenografts in castrated hosts. LNCaP cells were inoculated subcutaneously into male nude mice with weekly monitoring of serum PSA. Once serum PSA values reached 75-100 ng/mL, the animals were castrated and injected daily intraperitoneally with carbidopa (25 mg/kg) [Inhibitor group] or vehicle consisting of 10% DMSO in PBS [Control group]. Each animal group contained a minimum of 5 mice, with a range of 5-6 mice. Measured serum PSA values were normalized to pretreatment values (set at 100%) to obtain the mean percentage PSA of pre-treatment (±SEM). Statistical analysis was performed using the Student's t-test (two-sample equal variance) with JMPIN statistical software (Version 4.0.2, SAS Institute Inc.); $^a$p<0.05 as compared to the corresponding value for the inhibitor group (+carbidopa).

FIG. 12B—Effect of carbidopa DDC inhibitor on parental LNCaP xenograft tumour growth in castrated mice. LNCaP cells were inoculated subcutaneously into male nude mice with weekly monitoring of serum PSA and tumour volumes. Once serum PSA values reached 75-100 ng/mL, the animals were castrated and injected daily intraperitoneally with carbidopa (25 mg/kg) [Inhibitor group] or vehicle consisting of 10% DMSO in PBS [Control group]. Each animal group contained a minimum of 5 mice, with a range of 5-6 mice. Measured tumour volume values were normalized to pretreatment values (set at 100%) to obtain the mean percentage tumour volume of pre-treatment (±SEM). Statistical analysis was performed using the Student's t-test (two-sample equal variance) with JMPIN statistical software (Version 4.0.2, SAS Institute Inc.); $^a$p<0.05 as compared to the corresponding value for the inhibitor group (+carbidopa).

FIG. 13A—depicts the effect of carbidopa treatment on serum PSA in androgen-independent C4-2 xenografts. Parental C4-2 cells were inoculated subcutaneously into castrated male nude mice with weekly monitoring of serum PSA. Once serum PSA values reached 75-100 ng/mL, the animals were injected intraperitoneally with carbidopa (25 mg/kg) or vehicle consisting of 10% DMSO in PBS. Each animal group contained a 2-3 mice. Measured serum PSA values were normalized to pretreatment values (set at 100%) to obtain the mean percentage PSA of pre-treatment (±SEM). The increase in PSA level was divided by the number of elapsed days (21 days) to determine PSA velocity for each group (linear regression slope analysis, GraphPad Prism 4); $^a$p<0.05 as compared to the control group (−carbidopa).

FIG. 13B—depicts the effect of carbidopa treatment on androgen-independent C4-2 xenograft tumour growth. Parental C4-2 cells were inoculated subcutaneously into castrated male nude mice with weekly monitoring of serum PSA and tumour volumes. Once serum PSA values reached 75-100 ng/mL, the animals were injected intraperitoneally with carbidopa (25 mg/kg) or vehicle consisting of 10% DMSO in PBS. Each animal group contained a 2-3 mice. Measured tumour volume values were normalized to pretreatment values (set at 100%) to obtain the mean percentage tumour volume of pre-treatment (±SEM). The increase in tumour volume was divided by the number of elapsed days (21 days) to determine growth rates for each group (linear regression slope analysis, GraphPad Prism 4); $^a$p<0.05 as compared to the control group (−carbidopa).

FIG. 14—depicts the role of DDC-AR Coactivation in Neuroendocrine Trans-differentiation of Prostate Cancer Adenocarcinoma Cells. In the early stages of prostate cancer, AR exhibits robust activity and is susceptible to hormone ablation therapy. However, this treatment can induce the trans-differentiation of a population of luminal epithelial-derived adenocarcinoma cells into the NE-phenotype, which is characterized by increased expression of DDC and other NE markers. The resulting intermediate NE trans-differentiated cell can possess both luminal and NE characteristics, providing the environment in which DDC can coactivate AR. Prolonged hormonal therapy may lead to complete loss of AR activity/expression in some NE-phenotype cells and result in extremely high levels of DDC expression. These AR-independent NE cells can maintain their own growth through production of mitogenic factors and are resistant to hormone ablation treatment.

All references cited herein are hereby incorporated by reference.

What is claimed is:

1. A method of treating a subject diagnosed with non-neuroendocrine prostate cancer, comprising administering to the subject a therapeutically effective amount of a dopa decarboxylase (DDC) inhibitor that inhibits enzymatic activity of dopa decarboxylase.

2. The method of claim 1, wherein the dopa decarboxylase inhibitor is selected from the group consisting of carbidopa (α-Methyl-dopahydrazine), MFMD (α-monofluoromethyldopa), NSD-1015 (3-hydroxybenzylhydrazine), Methyldopa (L-α-Methyl-3,4-dihydroxyphenylalanine), benserazide, and combinations thereof.

3. The method of claim 1, wherein the dopa decarboxylase inhibitor is carbidopa (α-Methyl-dopahydrazine).

4. The method of claim 1, wherein the dopa decarboxylase inhibitor is a combination of carbidopa (α-Methyl-dopahydrazine) and NSD-1015 (3-hydroxybenzylhydrazine).

5. The method of claim 1, wherein the decarboxylase inhibitor is administered in combination with other cancer therapeutic medication or intervention.

6. The method of claim 5, wherein the therapeutic intervention is androgen depletion therapy.

7. The method of claim 1, wherein the administration is intratumoral.

8. The method of claim 1, wherein the dopa decarboxylase (DDC) inhibitor is packaged in dosage unit form.

9. A method of inhibiting transdifferentiation of an androgen independent or androgen sensitive non-neuroendocrine prostate cancer cell to a neuroendocrine prostate cancer cell comprising exposing the non-neuroendocrine prostate cancer cell to a dopa decarboxylase inhibitor that inhibits enzymatic activity of dopa decarboxylase.

10. The method of claim 9, wherein the dopa decarboxylase inhibitor is selected from the group consisting of carbidopa (α-Methyl-dopahydrazine), MFMD (α-monofluoromethyldopa), NSD-1015 (3-hydroxybenzylhydrazine), Methyldopa (L-α-Methyl-3,4-dihydroxyphenylalanine), benserazide, and combinations thereof.

11. The method of claim 9, wherein the dopa decarboxylase inhibitor is carbidopa.

12. The method of claim 9, wherein the dopa decarboxylase inhibitor is a combination of carbidopa and NSD-1015.

13. A method of treating a subject diagnosed with a non-neuroendocrine prostate cancer, comprising administering to the subject a therapeutically effective amount of at least two dopa decarboxylase (DDC) inhibitors that inhibit enzymatic activity of dopa decarboxylase.

14. The method of claim 13, wherein the dopa decarboxylase inhibitors are selected from the group consisting of carbidopa (α-Methyl-dopahydrazine), MFMD (α-monofluoromethyldopa), NSD-1015 (3-hydroxybenzylhydrazine), Methyldopa (L-α-Methyl-3,4-dihydroxyphenylalanine), benserazide, and combinations thereof.

15. The method of claim 13, wherein one of the dopa decarboxylase inhibitors is carbidopa (α-Methyl-dopahydrazine).

16. The method of claim 13, wherein the dopa decarboxylase inhibitors are carbidopa (α-Methyl-dopahydrazine) and NSD-1015 (3-hydroxybenzylhydrazine).

17. The method of claim 13, wherein the decarboxylase inhibitors are administered in combination with other cancer therapeutic medication or intervention.

18. The method of claim 17, wherein the therapeutic intervention is androgen depletion therapy.

19. The method of claim 13, wherein the administration is intratumoral.

20. The method of claim 13, wherein the dopa decarboxylase (DDC) inhibitors are packaged in dosage unit form.

21. A method of treating a patient diagnosed with a non-neuroendocrine prostate cancer comprising administering a dopa decarboxylase inhibitor that inhibits enzymatic activity of dopa decarboxylase to prostate cancer cells, in an amount effective to decrease the affinity of androgen receptors for androgen in the prostate cancer cells.

22. The method of claim 21, wherein the dopa decarboxylase inhibitor is selected from the group consisting of carbidopa (α-Methyl-dopahydrazine), MFMD (α-monofluoromethyldopa), NSD-1015 (3-hydroxybenzylhydrazine), Methyldopa (L-α-Methyl-3,4-dihydroxyphenylalanine), benserazide, and combinations thereof.

23. The method of claim 21, wherein the dopa decarboxylase inhibitor is carbidopa.

24. The method of claim 21, wherein the dopa decarboxylase inhibitor is a combination of carbidopa and NSD-1015.

25. The method of claim 21, wherein the decarboxylase inhibitor is administered in combination with other cancer therapeutic medication or intervention.

26. The method of claim 25, wherein the therapeutic intervention is androgen depletion therapy.

27. The method of claim 1, wherein the dopa decarboxylase (DDC) inhibitor is a structural analogue of dopa.

28. The method of claim 9, wherein the dopa decarboxylase (DDC) inhibitor is a structural analogue of dopa.

29. The method of claim 13, wherein the dopa decarboxylase (DDC) inhibitors are structural analogues of dopa.

30. The method of claim 21, wherein the dopa decarboxylase (DDC) inhibitor is a structural analogue of dopa.

31. The method of claim 1, wherein the subject is human.

32. The method of claim 13, wherein the subject is human.

33. A method of treating a subject diagnosed with non-neuroendocrine prostate cancer, comprising administering to the subject a therapeutically effective amount of a means for inhibiting the enzymatic activity of dopa decarboxylase.

34. The method of claim 1, consisting of administration of a therapeutically effective amount of a dopa decarboxylase (DDC) inhibitor that inhibits enzymatic activity of dopa decarboxylase selected from the group consisting of carbidopa (α-Methyl-dopahydrazine), MFMD (α-monofluoromethyldopa), NSD-1015 (3-hydroxybenzylhydrazine), Methyldopa (L-α-Methyl-3,4-dihydroxyphenylalanine), benserazide, and combinations thereof.

35. The method of claim 9, consisting of administration of a therapeutically effective amount of a dopa decarboxylase (DDC) inhibitor that inhibits enzymatic activity of dopa decarboxylase selected from the group consisting of carbidopa (α-Methyl-dopahydrazine), MFMD (α-monofluoromethyldopa), NSD-1015 (3-hydroxybenzylhydrazine), Methyldopa (L-α-Methyl-3,4-dihydroxyphenylalanine), and benserazide, and combinations thereof.

* * * * *

UNITED STATES PATENT AND TRADEMARK OFFICE
CERTIFICATE OF CORRECTION

PATENT NO. : 8,324,280 B2
APPLICATION NO. : 12/537895
DATED : December 4, 2012
INVENTOR(S) : Wafa et al.

It is certified that error appears in the above-identified patent and that said Letters Patent is hereby corrected as shown below:

Column 34, Claim 35, Lines 52-59 should read: --The method of claim 9, consisting of administration of a therapeutically effective amount of a dopa decarboxylase (DDC) inhibitor that inhibits enzymatic activity of dopa decarboxylase selected from the group consisting of carbidopa (α-Methyl-dopahydrazine), MFMD (α-monofluoromethyldopa), NSD-1015 (3-hydroxybenzylhydrazine), Methyldopa (L-α-Methyl-3,4-dihydroxyphenylalanine), benserazide, and combinations thereof.--

Signed and Sealed this
Fifth Day of February, 2013

Teresa Stanek Rea
*Acting Director of the United States Patent and Trademark Office*